(12) United States Patent
Welsh

(10) Patent No.: US 10,253,363 B2
(45) Date of Patent: Apr. 9, 2019

(54) MATERIALS AND METHODS TO ANALYZE RNA ISOFORMS IN TRANSCRIPTOMES

(71) Applicant: Vaccine Research Institute of San Diego, San Diego, CA (US)

(72) Inventor: John Welsh, Encinitas, CA (US)

(*) Notice: Subject to any disclaimer, the term of this patent is extended or adjusted under 35 U.S.C. 154(b) by 142 days.

(21) Appl. No.: 15/042,161

(22) Filed: Feb. 12, 2016

(65) Prior Publication Data
US 2017/0058342 A1 Mar. 2, 2017

Related U.S. Application Data

(60) Provisional application No. 62/115,738, filed on Feb. 13, 2015.

(51) Int. Cl.
*C12Q 1/68* (2018.01)
*C12Q 1/6874* (2018.01)
*C12Q 1/6806* (2018.01)
*C12Q 1/6832* (2018.01)

(52) U.S. Cl.
CPC ......... *C12Q 1/6874* (2013.01); *C12Q 1/6806* (2013.01); *C12Q 1/6832* (2013.01)

(58) Field of Classification Search
CPC ... C12Q 1/6874; C12Q 1/6806; C12Q 1/6832
USPC ........................................................ 506/16
See application file for complete search history.

(56) References Cited

U.S. PATENT DOCUMENTS

| | | | | |
|---|---|---|---|---|
| 6,096,563 | A * | 8/2000 | Hajizadeh | G01N 33/54313 435/7.1 |
| 8,209,130 | B1 * | 6/2012 | Kennedy | C12Q 1/6869 435/6.11 |
| 2003/0049599 | A1 * | 3/2003 | Kamb | C12N 15/1065 435/4 |
| 2011/0257031 | A1 * | 10/2011 | Bodeau | C12N 15/1065 506/9 |
| 2013/0274117 | A1 * | 10/2013 | Church | C12Q 1/6869 506/4 |

OTHER PUBLICATIONS

Fan et al., Combinatorial labeling of single cells for gene expression cytometry, Science 34:828 and 1258367-1 through 1258367-1 (Feb. 6, 2015).
Fu et al., Molecular indexing enables quantitative targeted RNA sequencing and reveals poor efficiencies in standard library preparations, PNAS 11(5):1891-1896 (Feb. 4, 2014).
(Continued)

*Primary Examiner* — Karla A Dines
(74) *Attorney, Agent, or Firm* — David R Preston

(57) ABSTRACT

The present invention includes, but is not limited to, methods, assays, and compositions for preparing libraries of nucleic acid molecules from biological samples, and for detecting and measuring the abundances of nucleic acid molecules, including RNA and DNA. The methods, assays, and compositions of the present invention provide in whole or in part for the detecting and measuring the abundances of nucleic acid molecules, and particularly but not limited to those nucleic acids that have structures that cannot be determined reliably by routine alignment to a reference sequence or concatenation of smaller sequences by matching homologous ends.

26 Claims, 5 Drawing Sheets

(56) References Cited

OTHER PUBLICATIONS

Hiller et al., Identifiability of isoform deconvolution from junction arrays and RNA-SEQ, Bioinformatics, 25(23):3056-3059 (2009).
Jiang and Wong, Statistical inferences for isofoun expression in RNQ-Seq, 25(8):1026-1032 (2009).
Lacroix et al., Exact transcriptome reconstruction from sort sequence reads, WABI 2008, LNBI 5251, pp. 50-63 (2008).
Tilgner et al., Comprehensive transcriptome analysis using synthetic long-read sequencing reveals molecular co-association of distant splicing events, Nature Biotechnology, 33(7): 736-742 (Jul. 2015).
Zheng et al., Haplotyping germline and cancer genomes using high-throughput linked-read sequencing, Nature Biotechnology, 34(3):303-311 (Mar. 2016).

\* cited by examiner

FIG. 1A

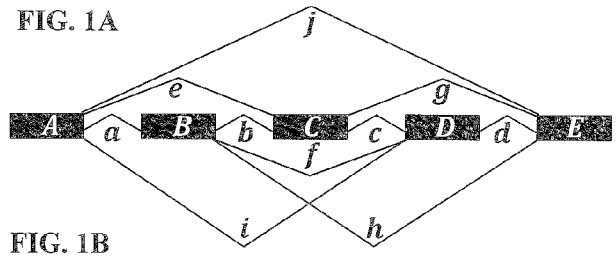

Three equations in 4 unknowns:

$$T1\begin{pmatrix}1\\0\\0\end{pmatrix} + T2\begin{pmatrix}0\\1\\0\end{pmatrix} + T4\begin{pmatrix}0\\0\\1\end{pmatrix} + T6\begin{pmatrix}-1\\1\\1\end{pmatrix} = \begin{pmatrix}15\\105\\35\end{pmatrix}$$

Full length cDNA

MATERIALS AND METHODS TO ANALYZE RNA ISOFORMS IN TRANSCRIPTOMES

The present application claims benefit of priority to U.S. Provisional application Ser. No. 62/115,738, filed Feb. 13, 2015, entitled "Materials and Methods to Analyze RNA Isoforms in Transcriptomes," which is incorporated by reference in its entirety herein.

TECHNICAL FIELD

The present invention generally relates to the field of molecular biology, and more specifically to the field of gene expression analysis using high-throughput sequencing of RNA molecules to generate sequence reads. The present invention addresses the problem of reconstructing valid RNA isoform models from short sequence reads, and more specifically the invention provides, in part, methods to construct cDNA libraries, which, when sequenced, can provide sufficient information to determine certain RNA isoform models. The present invention also applies to the field of DNA sequencing, and more specifically the invention provides, in part, methods to construct DNA libraries, which, when sequenced, can provide sufficient information to determine certain DNA sequence models.

BACKGROUND

Current methods for RNA-seq library preparation attempt to uniformly sample all sequences across every RNA molecule, optimally with sufficient overlap to allow de novo reassembly of the RNA sequences from which they derive, or alternatively, to allow inference of RNA sequence by alignment with reference sequences. RNA-seq methods use various length nucleic acid molecules, and from these molecules, generate sequence reads of varying length. Some methods can generate short sequence reads of ~125 nt in length, and can include almost every sequence in the transcriptome, including splice junctions (1, 2). These methods are referred to herein as "standard RNA-seq library preparation methods" or the "standard methods". These standard methods have in common that the libraries of sequences that they contain correspond to the sequences of genes, and more directly, from the messenger RNAs (i.e. mRNAs) transcribed from genes. The libraries include RNA sequences from DNA regions that are not necessarily considered to be genes, including but not limited to microRNAs, short interfering RNAs, long non-coding RNAs, and others. Similar libraries contain sequences directly obtained from DNA, including but not limited to genomic DNA, organelle DNA, mitochondrial DNA, chloroplast DNA, pathogen DNA, commensal organism DNA, viral DNA, parasite DNA, and symbiotic organism DNA. The term "standard methods" will be used herein to refer to both RNA and DNA library preparation methods.

One common goal of nucleic acid sequencing is to quantify the presence of nucleic acid molecules, and another common goal is to reconstruct a partial, a nearly complete, or a complete representation of a target molecule. This is typically done by concatenating partial sequence reads according to shared homology. Alternatively, a partial, a nearly complete, or a complete representation of a target molecule can often but not always be assembled by homology to one or more reference sequences.

Some existing standard methods for high-throughput nucleic acid sequencing produce sequence "reads" that are short relative to the length of the molecules being sequenced and relative to molecular features of interest. The molecules being sequenced will be referred to herein as "target molecules".

As an example of what may be encountered using other sequencing technologies, when a sequencing method gives reads of about 100 nt, alternative features that are greater than 100 nt apart can give rise to computational ambiguity.

As a further example of what may be encountered using other sequencing technologies, in certain cases, short sequence reads including sequences from one exon, sequences from two exons and an intervening splice junction, or sequences from two or more exons and two or more splice junctions can be insufficient to reconstruct or infer the structures of the molecules from which they derive. As a further example, target DNA molecules sometimes contain alternative regions that are flanked by shared regions, such that sequence reads are too short to reconstruct the molecules from which they derive.

Computational problems arise when using short sequence reads to reconstruct target molecule sequences. Complications in analysis of RNA arise due to differential promoter usage, splicing isoforms, alternative polyadenylation, and opposite strand transcription. Genes often encode complex patterns of isoforms due to alternative splicing (2-4). Algorithms developed to identify isoform models from short sequence reads produced by RNA-seq data alone are limited to cases in which the proportions of isoforms can be determined or estimated algebraically from exon and splice junction frequencies, and these limitations have been discussed (5-13). Other approaches for assembling isoform models exist, including pathway and probability models. In most cases, the correct isoform model is indistinguishable from incorrect models when linear equations that relate the frequencies of isoforms to the frequencies of exons and exon junctions are under-constrained, in which case, the correct model is considered unidentifiable. This constraint is not circumvented by pathway or probability approaches to isoform model identification. In the sense used here, unidentifiability is not related to errors or inadequacies in measurement. There exist cases in which a gene produces minor, or rare, isoforms which may or may not be of interest, and which may or may not be detected. In such cases, there may be a preferred model in which some minor isoforms are ignored and which comprises an acceptable approximation to the correct model. A preferred model is, therefore, an approximation to the correct model in which various isoforms, usually rare isoforms, may be excluded from analysis. A preferred model need not account for all isoforms, such as minor or rare isoforms. As is the case for the correct model in which all isoforms are accounted for, a preferred model is rendered unidentifiable when the equations that relate the frequencies of isoforms to the frequencies of exons and exon junctions are under-constrained. In such cases, both the correct and preferred models are unidentifiable. For example, when there are five exons, ABCDE, and the actual isoforms are ABCDE, ACDE, ABCE, and ACE, and are present in measurable quantities, neither the correct model, nor the preferred model can be identified from short sequence reads. FIG. 1 shows that an algebraic model based on read frequencies for a hypothetical gene with this isoform structure has an infinite number of solutions. Some RNA-seq methods produce possibly non-overlapping sequences from both ends of the library molecules, producing so called "paired end reads". Paired end reads do not solve the isoform problem (13). In real data, measurement error can or will cause convergence on a fictitious model. FIG. 1 is generally representative of the state of the art prior to the present invention and problems associated therewith.

This is an important problem to be addressed, given the potential phenotypic consequences of changes in alternative splicing in normal development and pathology. As a non-limiting example, in normal cortical development, the Numb gene produces isoforms numb1 and numb3 in undifferentiated cortical progenitors, whereas isoforms numb2 and numb4 are expressed during differentiation; re-expression of numb1 or numb3 resulted in alteration of neuronal development (14). As another non-limiting example, alternative isoforms of androgen receptor, often caused by mutation, lead to constitutively active androgen receptor, which is thought to drive cancer cell proliferation in castration-resistant prostate cancer (15).

Hiller et al. (6) considered 2256 genes known to yield multiple isoforms and found that only 68 genes (3%) lead to unidentifiable models using these identifiability criteria. Hiller et al. (6) pointed out that most of the 68 failed models contained an isoform with an exon flanked by two alternative splicing events, i.e. isoforms such as ACE, and that this becomes a significant problem when there are 5 or more isoforms. At that time, RefSeq associated only 133 of 2256 genes with 5 or more isoforms, whereas, currently, three times as many genes, 405 of 2256 genes, are associated with 5 or more isoforms, suggesting that about 9% of genes have isoform structures that cannot be modeled, but this estimate could easily increase as knowledge of the transcriptome increases.

BRIEF DESCRIPTION OF THE FIGURES

FIG. 1 Depicted is one aspect of an example of the problem addressed by the present invention of an isoform model that cannot or reasonably cannot be solved using short sequence reads generated using the standard approach. FIG. 1a depicts the exon structure of a hypothetical gene. FIG. 1b depicts possible alternative isoforms, in which the first and last exons are held invariant. FIG. 1c depicts a matrix representation of the problem. FIG. 1d depicts an algebraic solution of the matrix. In this example, isoforms T1, T2, T4 and T6 (depicted in FIG. 1a) represent most of the mass, and these have the proportions of 20:100:30:5, respectively. As depicted in FIG. 1c, the numbers in the last column of the augmented matrix, i.e. the column following the vertical line, are the calculated expected ratios of each splice junction and exon, which are labeled a-j for the splice junctions, and A-E for the exons. This augmented matrix can be converted into reduced row-eschelon form (right-hand matrix in FIG. 1c), which can be translated into the equation in FIG. 1d. This equation is a matrix form for 3 simultaneous equations in 4 unknowns (i.e. the unknowns are T1, T2, T4 and T6), which indicates that even a frill accounting of features a-j and A-E is insufficient to fully constrain the system.

FIG. 2 Depicted is one general example of one aspect of the present invention relating to generation of barcoded beads. One strategy for quantifying RNA isoforms requires that each bead contain, preferably, hundreds or more of copies of the same randomly chosen barcode sequence, but that different beads preferably contain different barcodes. The ratio of the total number of barcodes and the total number of beads can be adjusted.

FIG. 4. Depicted is one general example of the present example relating to uses of surfaces, including bead surfaces, having oligonucleotides with the structure SURFACE-5'-Spacer-Linker-Zip-Barcode-N(n)-3'. Note the left-to-right order of the 5' and 3' symbols, which differs from their orientation in FIG. 3. In this method, the beads are used as surfaces for bridge PCR. This can be done in emulsion or in packed beads with inert spacer beads added in excess. The invention also provides for the synthesis or physical placement of barcoded random primers in different positions on a larger surface, including but not limited to glass, ceramic, polymer surfaces, or surfaces comprising other materials. An aspect of these oligonucleotides is the free 3' end of the barcoded random primer. This is interesting because enzymes that perform DNA and RNA synthesis by primer extension can only extend from a 3' end.

SUMMARY

Figure 2A:
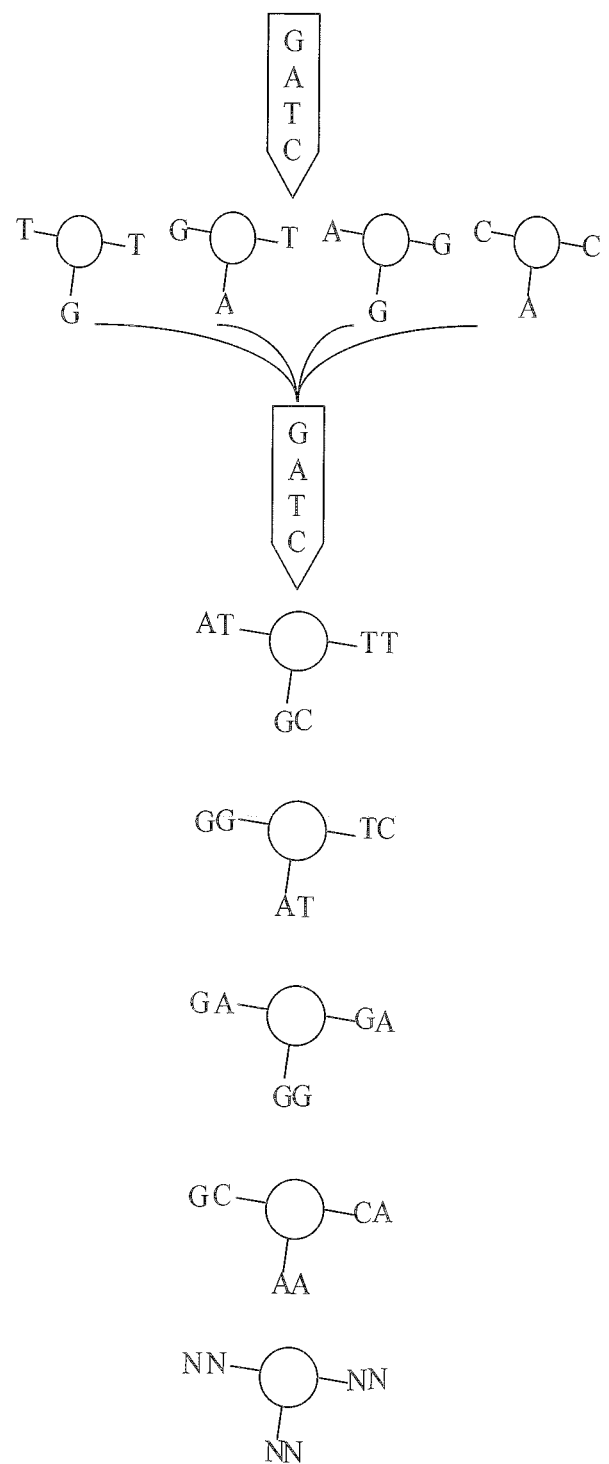
FIG. 2a depicts the usual scheme for generating random sequences: this is how random hexamers used in random priming are typically made.

The present invention recognizes that short sequence reads cannot always be reassembled into the sequences of the molecules from which they derive.

A first aspect of the present invention is a library of surfaces modified to host oligonucleotides that contain a randomized or partially randomized region attached to a barcode region, wherein each surface contains a single barcode or barcode set, and optionally, additional sequences to reduce steric effects near the surface, to aid in library preparation, and to aid in multiplex analysis.

A second aspect of the present invention is a method to prepare surfaces having oligonucleotides with these characteristics.

A third aspect of the present invention is a method to use such a library of modified surfaces to generate barcoded random primers in the vicinity of the surface to prime barcoded randomly primed synthesis of nucleic acids in the vicinity of the surface, such as within the confines of an emulsion droplet or other vessel. Sequences of the resulting products can or will be grouped according to the sequences of barcode region. These grouped sequences can or will be assembled into the correct or nearly correct sequences of the template molecules.

A fourth aspect of the present invention is a method to use such a library of modified surfaces to randomly prime synthesis directly on oligonucleotides attached to the surface, and to amplify and sequence these products. In this aspect of the present invention, sequences of the resulting products can or will also be grouped according to the sequences of barcode region. These grouped sequences can or will be assembled into the correct or nearly correct sequences of the template molecules.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the laboratory procedures in cell culture, chemistry, microbiology, molecular biology, cell science and cell culture described below are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

A "short sequence read" corresponds to a determination of the nucleotides in a target nucleic acid molecule in the order in which they occur and can or will include only a part of the target molecule, and can or will exclude other parts of the target molecule. The word "short" in this context does not necessarily correspond to a fixed length. Short sequence reads can or will lack information required to reconstruct the target molecule by concatenation of homologous regions, homology to a reference sequence or a combination thereof. Current sequencing methods can produce reads of various lengths. Some sequencing methods, including but not limited to those that use physical separation of molecules of different sizes, can or will produce sequence reads ranging from one nucleotide to more than a thousand nucleotides. Alternatively, some sequencing methods produce shorter reads consisting or, preferably, 1 to 50 nucleotides, 1 to 100 nucleotides, 1 to 200 nucleotides and longer, and the possible lengths may increase as technology improves. While short read lengths can or will result in analysis ambiguities when deducing or inferring the sequences of larger molecules from which they can or will derive, such methods have advantages due to the large number of such reads that can be generated at low cost. The lengths of so called "short reads" have increased over time, and the number of reads has also increased. There is a need for analysis of sequencing data from sequence reads that are shorter than the distance between alternative splicing sites in a target molecule or other alternative sequence features whose common molecular origin cannot be inferred or deduced from the given lengths of the sequence reads. Thus, whether a sequence read is too short to allow for the reconstruction of a target molecule depends on the length of the read and on the possible structures of the target molecule. For very large mRNAs, which can be thousands, tens of thousands, or even hundreds of thousands of nucleotides in length, the alternative splicing sites that give rise to computational ambiguity can or will be hundreds, thousands, tens of thousands, or hundreds of thousands of nucleotides apart, in which case reads that fail to span the alternative sites are, by definition, too short.

The present application uses the term "short sequence reads" to refer to sequence reads from DNA or RNA that are too short to unambiguously reconstruct the sequences of the target molecules from which they are derived by methods based on homology, without reference to information in addition to homology with the target molecule sequence or an appropriate reference sequence or a combination thereof.

The term "sequence" refers to the sequential order of nucleotides in a nucleic acid molecule, or, depending on context, refers to a molecule or part of a molecule in which a particular sequential order of nucleotides exists.

The term "surface" has the generally understood meaning, and includes surfaces that are smooth or irregular. Surfaces can be of any size or shape, including surfaces that can be seen by the unaided eye as well as microscopic surfaces. Single molecules are understood to have surfaces, including the "surface" of a single nucleic acid molecule, and including the surface of the end of a nucleic acid molecule. A surface can be regular and smooth or irregular. Surfaces can be distributed on a larger surface, as non-limiting examples, the surfaces of the wells in a microtiter plate or the interior surfaces of capillaries. Surface can be in a test tube or other physical enclosure.

Herein, the term "barcode" refers to a sequence that can or will be used to group sequences of nucleic acid molecules. The present invention provides for attaching such barcode sequences to sequences of interest of naturally or synthetically derived nucleic acids. For example, sequences that undergo randomly primed synthesis in the proximity of a particular surface can or will be physically attached to the sequence of a barcode or to the sequences of a barcode set, as defined below.

The term "barcode set" refers to one or more barcodes that contain sequence features that distinguish them as distinct from other barcode sets. A barcode set can contain unrelated sequences, or sequences that are in some manner related, such as sequences in which there are errors or intentional differences introduced during their synthesis. As a non-limiting example, one barcode in a barcode set can have the sequence GATCAAAA, in which the GATC portion of the sequence in defines the barcode set, and a barcode within the set but distinguishable from the first can have the sequence GATCTAAA. As a second non-limiting example, a barcode set can have a sequence such as XRRXXX, in which X indicates a defined nucleotide, guanine (G), adenine (A), thymine (T), cytosine (C), uracil (U), and inosine (I), or other nucleotide, and R indicates any purine nucleotide. These nucleotides will be referred to by their single letter codes, G, A, T, C, U, and I, throughout.

The term "polonies" refers to polymerase colonies, as described by Mitra et al. (16).

The term "complexity" refers to the total number of nucleotides that exist in unique strings assuming a minimum string length, and corresponds to the ordinary meaning of the term in the art.

The term "isoform", when applied to RNA, refers to RNA molecules that share some portion but not all of their sequence, and derive from the same gene. For RNA, the sequences can differ due to alternative promoter usage or post-transcriptional processing, such as splicing and polyadenylation. With respect to RNA, we also include differences due to mutations. When applied to DNA, isoform refers to two or more DNA regions preferably and substantially map to the same one or more chromosome region, and that share some portion but not all of their sequence. With respect to DNA, also included are differences due to mutations. Of particular but non-exclusive interest with respect to DNA isoforms are chromosomal rearrangements.

As it is understood in the art, the term "emulsion" refers to a preferably two-component solvent system in which droplets of one solvent are dispersed in the other. "Emulsion PCR" is in standard usage, and refers to polymerase chain reaction performed in the aqueous phase of an oil-water emulsion.

The term "reverse synthesis" or "reverse DNA synthesis", which is generally known in the art, refers to a chemical strategy for synthesizing oligonucleotides on a solid support, which proceeds in such a way that the 5' end of the oligonucleotide is attached to the surface and the oligonucleotide grows by addition to the 3' end.

The term "standard synthesis" or "standard DNA synthesis", which is generally known in the art, refers to the common chemical strategy for synthesizing oligonucleotides on a solid support which proceeds in such a way that the 3' end of the oligonucleotide is attached to the surface and the oligonucleotide grows by addition to the 5' end.

The term "contig" has general meaning in the art, and refers to contiguous partial sequences that can or may be assembled into a single sequence. Assembly is typically done by aligning sequences to each other or to a reference sequence, or a combination of both.

Other technical terms used herein have their ordinary meaning in the art that they are used, as exemplified by, but not limited to, a variety of technical dictionaries.

DETAILED DESCRIPTION

The present invention provides in part composition, articles of manufacture, apparatus, and methods to analyze RNA isoform or DNA structure. The invention provides in part for using oligonucleotides to introduce a barcode or barcodes into the products of randomly primed nucleic acid synthesis using single molecule templates by primer extension. The present invention provides for, preferably, the same barcode or barcode set to be colinear with preferably all of the extension products from a single molecule, and largely different barcodes or barcode sets to be collinear with preferably all of the extension products from other molecules. The resulting barcoded extension products can or will then be grouped according to their barcode sequence. As a barcode or barcode set preferably identifies the products from single molecules, assembly of the sequences from single molecules largely circumvents the problems encountered by standard library preparation methods relating to unambiguous model identification.

One aspect of the present invention provides in part for methods to attach barcodes to nucleic acid molecules by primed synthesis in which the barcode is attached to the randomized or partially randomized primer, and the subsequent preparation of the resulting barcoded nucleic acid molecules for sequencing. The invention provides in part for grouping the nucleic acid molecules with attached barcodes and inferring or deducing the sequences of the single molecule from which they derive.

The present invention includes in part instances in which the RNA molecules represented in the library are not considered mRNAs, such as but not limited to ribosomal RNAs, tRNAs and non-coding RNAs of various kinds, including but not limited to microRNAs, short interfering RNAs, and long non-coding RNAs. Considering as a non-limiting example, short sequence reads derived from mRNAs, short sequence reads can be assigned to the genes from which they derive, and with which they match by sequence matching. However, while short sequence reads from libraries made using the standard methods can usually be assigned to the correct gene by sequence matching, two or more short sequence reads cannot usually be assigned reliably to the same single RNA molecule simply by homology. In other words, two short sequence reads from the same gene can or will derive from different mRNAs derived from the gene. Genes that encode RNAs in multiple isoforms present a challenge: given a complete set of short sequence reads that span every exon and splice junction, certain alternative underlying RNA isoform models cannot be deconvoluted using data of this nature. This situation occurs when more than one isoform model can explain the frequencies of exon and junction short sequence reads, and it is mathematically unavoidable: ultimately, short sequence reads do not contain the information needed to unambiguously identify the correct isoform model for certain splicing patterns. A non-limiting example of a computational problem of this nature is illustrated in FIG. 1. The unidentifiability of certain RNA isoform models is an important problem to be addressed, given the potential phenotypic consequences of changes in alternative splicing in normal development and pathology. The present invention provides in part a method to solve this problem through unique strategies for RNA-seq library preparation and data analysis.

Such unidentifiable models can or will also occur with DNA from various sources, including DNA from various organisms that may exist in multiple structurally related alternatives, which can also be referred to as "isoforms". A non-limiting example includes pathogens that may exhibit high mutation rates, such that multiple mutations in the same pathogen genome cannot be determined unambiguously to belong to the same molecule. Another non-limiting example includes analysis of a population of organisms in which multiple alternative genome arrangements may exist. The present invention provides in part a method to preserve information that allows the co-occurrence of sequence information in the same molecule to be determined.

In one embodiment of the present invention, a single barcode is associated with multiple short sequence reads from the same RNA or DNA molecule, such that, for example, each sequence read from a single molecule can be preferably substantially unambiguously assigned to that single molecule by reference to the barcode, and different barcodes are preferably associated with short sequence reads from every other individual RNA or DNA molecule.

For RNA molecules, each RNA molecule transcribed from the same gene preferably becomes associated with a different barcode. For DNA, related molecules may derive from the same cell, such as regions representing different alleles, repetitive elements, or gene family members, or related molecules may derive from different alleles, repetitive elements, or gene family members from different cells.

In another embodiment of one aspect of the present invention, more than one barcode, forming a set of barcodes or "barcode set" (defined above), is associated with multiple short sequence reads from the same RNA or DNA molecule, in such a way that each sequence read from a single molecule can be preferably substantially unambiguously assigned to that single molecule by reference to the barcode set and different barcode sets are preferably associated with short sequence reads from every other individual RNA or DNA molecule.

The association of one molecule with one barcode or barcode set can be done by primed synthesis of DNA using barcoded primers in such a manner that each RNA or DNA molecule is preferably exposed to a single barcode, or barcode set, during primed DNA synthesis. More than one barcode can or will permissible. The primed synthesis of DNA can be randomly primed synthesis, partially randomly primed synthesis, which occurs when the priming sequence is not fully randomized, or by targeted primed synthesis, in which the priming sequences are targeted to specific target sequences. This method produces molecule-specific collections of barcoded DNAs which, upon high throughput sequencing, can be aligned to discover the specific structural details of RNA isoforms on a molecule-by-molecule basis. This approach addresses the isoform model identifiability problem. This method also addresses limitations of the parsimony assumption, in cases where the most parsimonious solution is not necessarily the correct solution.

In another embodiment of an aspect of the present invention, the target molecules to be sequenced comprise DNA molecules or fragments of DNA molecules or RNA molecules or fragments of RNA molecules, or from any organism, and molecule-specific barcode or barcodes are similarly associated with short sequence reads from these nucleic acid target molecules.

The present invention provides for, in part, modified surfaces having the structure SURFACE-3'-Spacer-Linker-Zip-Barcode-N(n)-5' or the structure SURFACE-5'-Spacer-Linker-Zip-Barcode-N(n)-3'. In this shorthand notation, the term "SURFACE" refers broadly to surfaces including but not limited to beads, indentations or wells in plates, test tubes, capillaries, or other physical constructs that have surfaces, that can or will have various sizes, shapes, and can be formed from various materials. As a non-limiting example, a surface can be a single well in a microtiter plate or a similarly isolated region or location in a larger construct.

One aspect of the present invention provides for, in part, a surface, designated herein as "SURFACE", having a wide range of possible sizes including surfaces that range in size preferably from between about 1 nanometer to about 1 micrometer, about 1 micrometer to about 10 micrometers, about 10 micrometers to about 100 micrometers, about 100 micrometers to about 1 millimeter in the longest dimension, and can or will be larger. The present invention provides in part surfaces having any shape, including but not limited to spheres, spheroids, ellipsoids, regular polyhedral, filaments, irregular shapes, random shapes, toroids, knots, mobius strips, and defined shapes of any structure, including but not limited to surfaces constructed by lithography, two-dimensional printing, or three-dimensional printing, or by self-assembly, cutting, stamping, scraping, molding, precipitating, polymerizing, depositing, disrupting, crosslinking, or coagulating. The present invention provides in part for SURFACE composed of various materials including but not limited to glass, controlled pore glass, polymers, composite materials, magnetic material, biomaterials such as nucleic acids, condensed nucleic acid particles, crosslinked nucleic acids, proteins, protein aggregates, or mixtures thereof.

In another aspect, the present invention provides in part one or more SURFACE upon which oligonucleotides comprising 3'-Spacer-Linker-Zip-Barcode-N(n)-5' or 5'-Spacer-Linker-Zip-Barcode-N(n)-3' as they appear in SURFACE-3'-Spacer-Linker-Zip-Barcode-N(n)-5' or the structure SURFACE-5'-Spacer-Linker-Zip-Barcode-N(n)-3' are printed in or otherwise attached to spatially distinct positions. This spatial separation can include separate reaction locations for oligonucleotides synthesized using patterned surface chemistry, including but not limited to ink jet reagent delivery methods, such as but not limited to those used to synthesize micromays, methods based on photolithography, and methods that use microfluidics. It is to be understood that the term oligonucleotide can include deoxyribonucleotides or ribonucleotides or a combination thereof, and can include modified bases, as well as modified linkages between bases.

A sequence designated "Spacer" is included optionally to relieve steric hindrance, linker is an optionally included adaptor sequence, zip is an optionally included zip-code sequence to allow multiple biological samples or repeats of the same biological sample to be included in the same sequencing reaction or sequencing analysis location. The nature of the sequencing analysis location differs from one high throughput sequencing platform to the next, and the present invention provides in part composition, articles of manufacture, apparatus, and methods of making and using same, and combinations thereof, to analyze RNA isoform or DNA structure irrespective of the shape of the sequencing analysis location. The present invention provides in part for sequencing analysis locations of various configurations. The present invention provides in part for a sequencing analysis location that has the shape of a physical channel. The present invention provides in part for sequencing analysis locations having a round or square surface area (such as a reaction chamber made by lithography, MEMS, etching, machining, molding, or stamping). The present invention provides in part for a sequencing analysis location that has an area accessed by microfluidics, a volume, or the surface of a bead or other surface that is fixed on a larger surface.

One aspect of the present invention provides in part composition, articles of manufacture, apparatus, and methods of making and using same, and combinations thereof to analyze RNA isoform structure or DNA structure from short sequence reads that are produced by any type of sequencing chemistry or enzymology that can or will produce sequences of the template nucleic acids linked to template molecule-specific "Barcodes".

In one aspect of the present invention, N(n) in SURFACE-3'-Spacer-Linker-Zip-Barcode-N(n)-5' and SURFACE-5'-Spacer-Linker-Zip-Barcode-N(n)-3', is preferably a randomized sequence n nucleotides long. In another aspect of the present invention, N(n) is preferably a partially randomized sequence n nucleotides long. In another aspect of the present invention, some or all of the nucleotides in N(n) are preferably defined.

Another aspect of the present invention provides, in part, for the surfaces of beads or other surfaces that can or will direct the synthesis of cDNA from specific genes or subsets of genes or DNA from one or more regions of genomic DNA, and differs from other existing strategies, in part, in the attachment of molecule-specific barcodes to the sequences belonging to the specific gene or subsets of genes, or DNA from one or more regions of genomic DNA. In part, the latter also addresses the problem of self-priming encountered in randomly primed PCR and other amplification strategies that employ random priming: by specifying preferably the 3' two nucleotides in an oligonucleotide used in primed synthesis, self-priming can or will be inhibited or reduced.

The sequence designated "Barcode" has unique properties. The present invention provides in part that the sequence of "Barcode" is well-defined or defined by its history of synthesis, or its method of synthesis. The present invention provides in part for a single barcode or barcode set on any single surface or subset of surfaces, but a different barcode or barcode set on other surfaces or subsets of surfaces.

As a non-limiting example, a library may contain $10^8$ beads and $4^6$ different barcodes, such that the $10^8$ beads can be divided into $4^6$ subsets according to the barcode, and each subset has a characteristic barcode, such as, for example, GATCGA. The present invention also provides in part for preferably a single barcode, or barcode set on any single surface location or a subset of surface locations, but different on other surface locations or subsets of surface locations, with these surfaces having any shape, such as any useful shape for the purpose at hand.

The number of barcodes is preferably large (>10), and possibly very large, (>1e+10), however this range is not intended to be limited and is for exemplar purposes only. The number of barcodes is an adjustable parameter, the choice of which can preferably be influenced by such variables as the complexity of the nucleic acid being analyzed and the complexity of possible isoform structures. Surfaces, including but not limited to the surfaces of solid support beads used in solid-state oligonucleotide synthesis methods, having the same synthetic history will or can have the same barcode, but surfaces that do not have the same synthetic history can or will have different barcodes.

Each surface can contain, for example, tens, hundreds, thousands, or more of such oligonucleotides. The barcodes can be added such that every barcode on a subset of the surfaces is the same, or of the same barcode set, while barcodes on different subsets of surfaces can overlap, but are preferably different. The present invention provides in part methods by which this can be accomplished by adding a single barcode base per channel of an oligonucleotide synthesis instrument having one channel per base type, including non-exclusively G, A, T, and C, combining, mixing and redistributing the support resin among the different channels, and repeating for the length of the barcode region. In some instruments, a "channel" corresponds to the vessel in which the DNA synthesis reaction takes place, and some instruments have 4 channels in which the four nucleotides, G, A, T, or C, are added to the growing oligonucleotide chain. It is to be understood that these reactions can be performed in other configurations, such as, but not limited to a single channel, test tube or other reaction vessel. It is also to be understood throughout that, while DNA comprises, typically four nucleotides designated G, A, T, and C, and RNA comprises, typically, four nucleotides designated G, A, U, and C, the present invention also provides for the use of other nucleotides, some of which are natural and some of which are man-made. The present invention also provides for, in part, the use of any natural or man-made nucleotide. There exist a variety of instruments for the synthesis of oligonucleotides on solid supports, such as surfaces, and older manual methods can be used. Surfaces with different histories can or will have different barcodes. Surfaces with the same history can or will have the same barcode such that all barcodes on a single surface can or will be identical, excluding differences due to synthetic errors, such as failure of a reaction to go to completion, and the randomized portion of the oligonucleotide represented by N(n). Also, differences in oligonucleotides can be introduced intentionally, such as inclusion of a barcode set rather than a single barcode. The present invention provides in pail for manipulation of the synthetic histories of subsets of surfaces such that surfaces may share part of their histories, leading to preferably known differences in barcodes on the same or different surface(s).

One aspect of the present invention provides in part for libraries of modified surfaces having structures such as SURFACE-3'-Spacer-Linker-Zip-Barcode-N(n)-5' or SURFACE-5'-Spacer-Linker-Zip-Barcode-N(n)-3' constructed by synthesizing the nucleic acid parts and attaching them, post-synthesis, to surfaces. Indeed, surfaces having oligo-d $(T)_n$ are in common use, as are surfaces having other sequences attached, and these can be manufactured both by direct synthesis on the surface or post-synthetic attachment.

Modified surfaces having the structure SURFACE-3'-Spacer-Linker-Zip-Barcode-N(n)-5' can be used to generate barcoded random primers by repeated primer extension from the Linker region, alternating with denaturation. When used in emulsion with enzymes that catalyze the templated synthesis of DNA, each surface can or will template the synthesis of one or more barcoded random primers, templated by the oligonucleotide or oligonucleotides attached to the surface or surfaces in the emulsion droplet. The present invention provides in part for synthesis of primers directed by structure SURFACE-3'-Spacer-Linker-Zip-Barcode-N(n)-5' using, for example, a thermostable polymerase and cycling the temperature, as in PCR. Alternatively, the present invention provides in part for synthesis of primers directed by structure SURFACE-3'-Spacer-Linker-Zip-Barcode-N(n)-5' using, for example, an RNA polymerase, using a promoter sequence in Spacer or Linker that can be converted to a functional promoter by hybridizing the complementary or nearly complementary strand. An arrangement in which every droplet contains one and only one surface cannot be achieved by simple random mixing, but the distribution of surfaces per droplet can be manipulated by changing the ratio of surfaces and the aqueous and emulsifying components. These barcoded random primers can or will prime synthesis of sequences found in the same emulsion droplet.

Emulsion PCR uses an oil-water emulsion in which reactants including buffers, nucleotides, oligonucleotide primers, enzymes, and other components are first dissolved in the aqueous phase, followed by emulsification with an oil phase. Emulsification can be achieved in a number of different ways, including but not limited to vortexing the mixture or injecting the aqueous component into the oil component through a needle, capillary, or other small pore. In one approach, the individual droplets of the emulsion can be forced into a channel, thereby producing a stream of aqueous reaction vessels bounded by the oil phase. Forming emulsion droplets is only one of many ways to achieve spatial separation of small reaction volumes. Other methods include but are not limited to forming droplets on a surface, placing reaction mixtures in capillaries, pits, channels, tubes, wells, indentations, or small-scale reaction vessels constructed using microfabrication technologies, three-dimensional printing, ink jet printing, milling, stamping, or lithography, or others or combinations thereof which can be referred to collectively as "spatial segregation methods".

The locations in spatial segregation methods in which reactions occur are referred to herein as "reaction vessels" or just "vessels" when they possess physical barriers to preferably limit mixing between reaction components. In some physical configurations, including but not limited to channels and microfluidic reaction vessels, amplification can be achieved using isothermal amplification, in which double-stranded molecules are denatured using a chemical solvent, for example, formamide, in preferably each amplification cycle.

Modified surfaces having the structure SURFACE-5'-Spacer-Linker-Zip-Barcode-N(n)-3' can be used with or without emulsion PCR to generate single molecule polonies attached to the surfaces, with multiple sampling from the input nucleic acid sequence, and each sample preferably tagged with the barcode from the surface.

One aspect of the present invention provides for, in part, the use of grouping of sequences according to the attached barcode. When two or more RNA or DNA molecules, or a combination thereof, extend from the oligonucleotides at a single analysis location, such as a single surface, the molecules are preferably first parsed into a group based on the attached barcode or barcode set. These groups are then preferably further parsed according to the gene-specific sequences present. The present invention provides in part a strategy to place isoforms from the same gene into different groups, and this provides that two or more template molecules are preferably associated with, respectively, different barcodes or barcode sets.

Isoform Identification Using Barcoded Random Primers Attached to Surfaces

The novel barcode structure of SURFACE-3'-Spacer-Linker-Zip-Barcode-$N_{(n)}$-5' can be prepared by standard DNA synthesis. A completely randomized hexamer using four nucleotides has the complexity $4^6=4096$. In general, a randomized sequence of the nucleotides G, A, T, and C containing n nucleotides has a complexity of $4^n$. Throughout, calculations of complexity of the form $N^n$ use N to represent the number of nucleotides that can be selected for each of n positions. If, for example, G, A, T, C and I were to be used, the number of possible sequences would be calculated as $5^n$. In one embodiment of the present invention, the complexity of barcodes in the surface library will be high (e.g. 1e+6), but each surface contains only a single barcode. Alternatively, different subsets of surfaces contain different barcode sets. In this strategy, the input material can be, preferably, full-length first strand cDNA when the sequence of interest is that of RNA, or DNA when the sequence of interest is DNA. During emulsion PCR, a copy of the DNA can or will made by random priming from barcoded random primers templated by the surface within PCR emulsion droplets or other spatial segregation method. The products are preferably not attached to the surfaces, and isolation of one DNA molecule from the next is spatial in emulsion droplets or other reaction vessels. These surfaces support a strategy for short read sequencing to generate short sequence reads in which every individual DNA molecule is represented in multiple randomly primed short sequence reads, each of which is tagged with a barcode unique to the individual molecule. Such data, if sufficiently complete, can be solved for the representations of most RNA isoforms or DNA isoforms, including those that cannot be solved using the standard library preparation methods regardless of completeness. Therefore this approach addresses an important technical problem that arises in RNA-seq studies based on short sequence reads that use standard RNA-seq library preparation methods, as well as problems that arise when sequencing DNA, especially DNA which contains different isoforms.

Isoform Identification Using Barcoded Reverse Random Primers Attached to Surfaces The barcode structure of SURFACE-5'-Spacer-Linker-Zip-Barcode-N(n)-3' can be prepared by reverse DNA synthesis. The complexity of barcodes in the surface library can or will be high (e.g. 1e+6) but each surface has oligonucleotides with preferably only a single barcode or single barcode set. In one embodiment, cDNA is made on the surfaces by oligo-dT(n) priming, and then the cDNA is randomly primed by barcoded oligonucleotides that are also attached to the surfaces. Alternatively, DNA, including but not limited to chromosomal DNA can be fragmented and tailed with poly-A using terminal transferase, poly-A-synthetase, or ligation and treated as cDNA. The products preferably remain attached to the surfaces. Isolation of one RNA, cDNA, or DNA molecule from the next is spatial, on packed surfaces. For example, when the surfaces comprise the surfaces of beads, molecules can or will be isolated from one another due to the fixed positions of the packed beads. The surfaces are further spatially isolated from each other by inert or relatively inert carrier surfaces, so that random priming of a DNA preferably only occurs on the surface to which the DNA is initially attached. For example, when the surfaces are provided by glass beads, silanized glass beads can or will be used as carriers, thereby preferably providing spatial separation between surfaces modified with oligonucleotides.

Isoform Identification Using Barcoded Random Primers that are Bound to Surfaces Embedded in One or More Larger Surfaces As described above and herein, the present invention provides in part for the use of modified surfaces, and additionally provides for several mechanisms by which the surfaces can be arranged to support library preparation in which individual RNA or DNA molecules are copied into short sequence reads that can be sequenced and grouped according barcodes or barcode sets that are introduced into the short sequences and sequence reads. The present invention also provides in part for physical isolation of modified surfaces by modification of surfaces in different locations on a larger, preferably fixed, surface. The present invention provides in part that this can or will be achieved by the printing of oligonucleotides on surfaces or by synthesizing the oligonucleotides on surfaces.

One aspect of the present invention provides for a way to construct libraries in which the modified surfaces, having structures SURFACE-3'-Spacer-Linker-Zip-Barcode-N(n)-5' or SURFACE-5'-Spacer-Linker-Zip-Barcode-N(n)-3', are located on a larger surface including, non-exclusively, a glass slide. For example, in one embodiment, individual oligonucleotides containing defined barcodes can be synthesized or printed on a larger surface by various methods, which have been used extensively to produce microarrays for nucleic acid analysis.

Another aspect of the present invention provides, in part, for individual spots on a larger surface that can or will be hydrophilic, and be surrounded by hydrophobic regions, allowing aqueous beads to form above and including the modified surfaces, but preferably excluding the intervening hydrophobic regions.

The present invention provides in part for the attachment of oligo-dT(n) to a subset of these oligonucleotides, giving SURFACE-5'-Spacer-Linker-Zip-Barcode-N(n)-T(n)-3'.

The present invention provides in part that these oligo-dT(n) terminated oligonucleotides initiate primed cDNA synthesis by reverse transcription in the poly A tails of mRNAs, with the resulting cDNAs attached to the SURFACE via the 5'-Spacer-Linker-Zip-Barcode-N(n)-T(n)-3' oligonucleotide, or remain unattached but isolated, as in microtiter plate wells. Further randomly primed PCR from nearby SURFACE-5'-Spacer-Linker-Zip-Barcode-N(n)-3' yields, preferably, random sampling of the mRNA sequences attached to any particular array node. Alternatively, the present invention provides in part for oligo-dT(n)

Isoform Identification Using Barcoded Random Primers in Wells

The present invention provides in part for methods to use barcodes to identify those short sequence reads that are templated by, or copied from, the same individual molecule, even though the several or many sequence fragments are no longer physically connected to each other. Therefore, the invention provides in part for the use of oligonucleotides having the structures 3%-Spacer-Linker-Zip-Barcode-N(n)-5' or 5'-Spacer-Linker-Zip-Barcode-N(n)-3' used in a format in which nucleic acid is amplified or copied by random priming methods in multiple analysis locations each of which harbors preferably an oligonucleotide having the structure 3'-Spacer-Linker-Zip-Barcode-N(n)-5' or 5'-Spacer-Linker-Zip-Barcode-N(n)-3' and having only one or a few barcodes or barcode sets. When the barcoded oligonucleotide 3'-Spacer-Linker-Zip-Barcode-N(n)-5' is used together with an oligonucleotide corresponding to Linker, the barcoded oligonucleotide serves as a generator of barcoded random primers. The present invention provides in part for methods in which such barcoded oligonucleotide primers are synthesized separately and physically placed individually or multiply into separate reaction vessels, the latter resulting in physically separated barcode sets. The reaction vessels may be of various physical configurations, including wells, capillaries, pits, channels, or vessels, made by any method, including but not limited to milling, stamping, or lithography, or other spatial segregation method.

For all or some of the above methods, the present invention also provides, in part, for amplification of nucleic acids by various methods, including but not limited to PCR, rolling circle amplification, linear amplification, and combinations thereof, before, during, or after attachment of barcodes. The present invention also provides, in part, for the inclusion of other nucleic acids, such as but not limited to oligonucleotide primers, and the inclusion of other enzymes, including but not limited to RNA polymerase, DNA polymerase, restriction endonucleases, carrier proteins, albumin, and single stranded binding proteins. The present invention also provides, in part, for the inclusion of small molecules, such as nucleotides, non-standard nucleotides, soaps, detergents, oils, salts, counter ions, fluorescent molecules, radionuclids, and other molecules, which may or may not influence the reactions or reaction products.

Preferred Aspects of the Present Invention

Overview

The present invention provides in part methods in which short sequence reads from the same RNA or DNA molecule are tagged with the same barcode. This barcode identifies the reads that comprise a single molecule contig. Contigs can or will be assembled by partial overlap within a collection, or by matching to a reference sequence, or a combination thereof. In the case of RNA, different barcodes preferably identify different contigs for RNAs from the same gene, and contigs from different genes are identified similarly by barcode and gene sequence. In the case of DNA, barcodes preferably identify sequences that belong to substantially the same or rearranged genomic region or regions.

The present invention provides in part for amplification of nucleic acids on surfaces, optionally on surfaces, including but not limited to surfaces of beads, or larger surfaces, and optionally in emulsion. Amplification of nucleic acid sequences on surfaces by PCR, emulsion PCR involving surfaces, including but not limited to beads, and randomly primed synthesis are all standard (17-21). The unique aspect of this invention concerns the design of the oligonucleotides that are fixed to the surfaces, including but not limited to beads, and methods that utilize this design. The present invention provides in part for:

1. a large library of surfaces, including but not limited to beads, containing tens, hundreds, thousands, or millions of surface-specific oligonucleotides containing barcode regions flanked by a linker region and a random primer region,
2. the oligonucleotides optionally containing a spacer region and a zip code region,
3. a method for producing such a library,
4. and uses thereof to identify the structures of nucleic acids from short sequence reads.

Alternatively, the present invention provides in part for:

1. a large library containing tens, hundreds, thousands, or millions of oligonucleotides containing barcode regions flanked by a linker region and a random primer region,
2. the oligonucleotides optionally containing a zip code region,
3. the oligonucleotides printed, deposited, or synthesized in spatially segregated locations,
4. and uses thereof to identify the structures of nucleic acids from short sequence reads.

One strategy calls for beads having the structure SURFACE-5'-Spacer-Linker-Zip-Barcode-N(n)-5'. Oligonucleotides synthesized using standard chemistry have their 3' end attached to the bead. Alternatively, a second strategy calls for surfaces, including but not limited to beads, \having the structure SURFACE-5'-Spacer-Linker-Zip-Barcode-$N_6$-3', wherein the oligonucleotide is synthesized by reverse synthesis. This bead synthesis strategy results in an extendable 3' end of the oligonucleotides. The two types of modified surfaces, which are beads or preferably beads, in this non-limiting example, are related by the method to build the barcode, which will be described in detail.

Although only one oligonucleotide is indicated in the shorthand notations, SURFACE-5'-Spacer-Linker-Zip-Barcode-$N_6$-3' and SURFACE-3'-Spacer-Linker-Zip-Barcode-$N_6$-5', it is to be understood that the surfaces can or will contain many oligonucleotides, up to hundreds of thousands or millions, and these different oligonucleotides on one bead can be identical, or nearly identical except for the optionally added N(n) region, which signifies a stretch of random sequence n nucleotides long, and except for intentional differences, including but not limited to intentional differences in barcodes, and except for synthesis errors, which are preferably minor.

Alternatively, the sequence N(n) may be partially specified, for example, the right-hand terminal one or more nucleotides may be fixed, while the remaining nucleotides are random.

In one aspect of the present invention, the oligonucleotide is not detached from the bead after synthesis. "Spacer" is a sequence whose purpose is to reduce steric hindrance. "Linker" is an adapter sequence that can be designed to make the library compatible with various sequencing methods, and Zip is a stretch of sequence that can or will be used to distinguish between RNA samples. N(n) is a random nonamer. These parts can or will be synthesized in the usual manner, using standard DNA synthesis chemistry. The synthesis of "Barcode" is more interesting: a subset of surfaces can or must be attached to a single barcode, or barcode set, and other subsets must be attached to different barcodes, or barcode set, although different subsets of surfaces can or will share some barcodes. The number of barcodes and barcodes that are shared depends on the objectives of the desired method, outcome intended, and purpose, and can or will range from zero to as high as 1e+6, and larger.

Figure 2B:
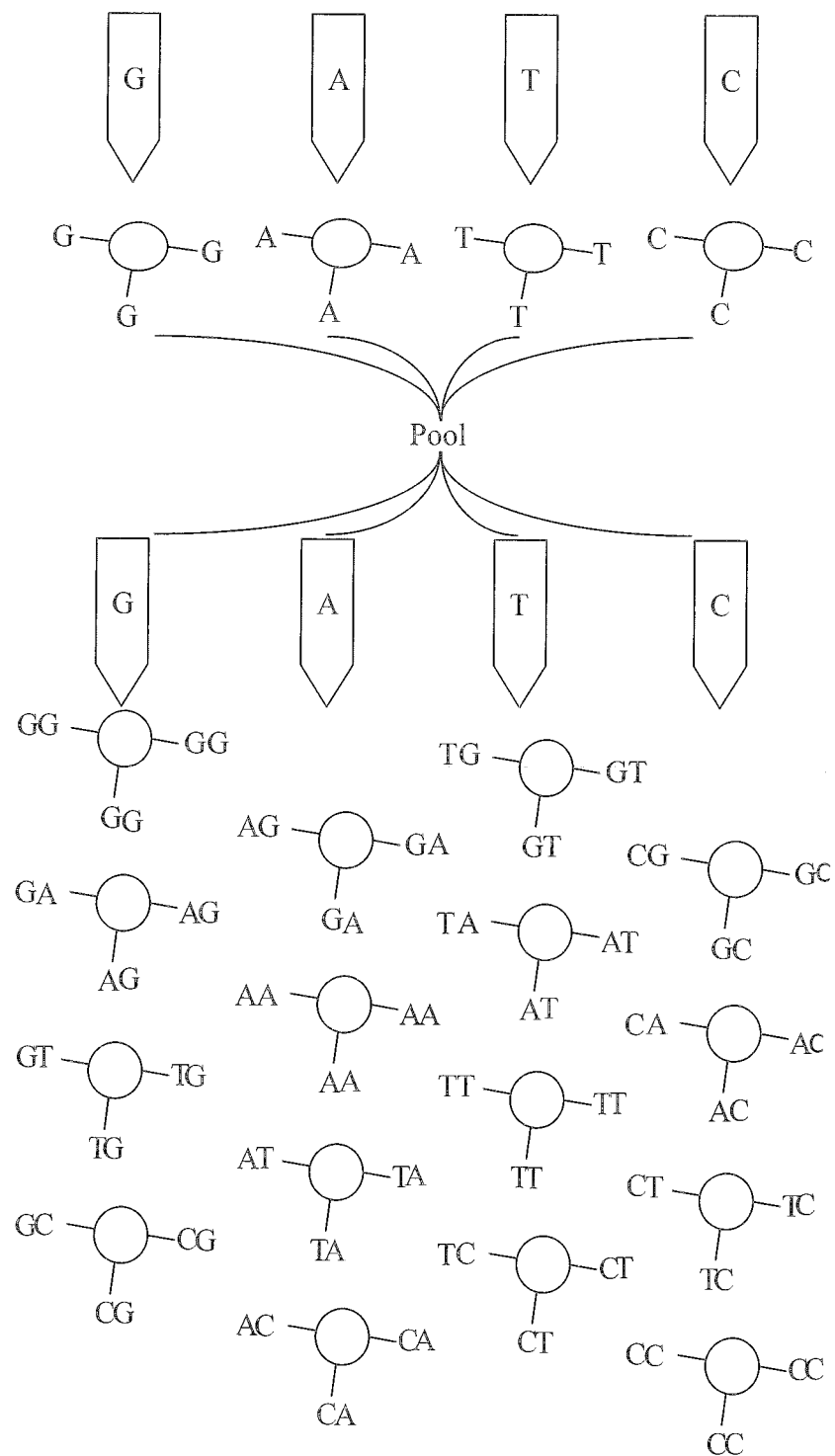
FIG. 2b depicts a scheme to attach unique oligonucleotides to many beads by synthesis, such that any single bead has attached, preferably, many copies of the same oligonucleotide or the same several oligonucleotides, whereas, while some beads have attached essentially the same oligonucleotide or several oligonucleotides, other beads have attached many copies of a different oligonucleotide or several different oligonucleotides. Different automated systems for DNA synthesis that may require different pooling approaches. For example, machines that perform synthesis in closed columns can or will require that the columns be opened in order to pool the beads at each step.
Figure 3A:
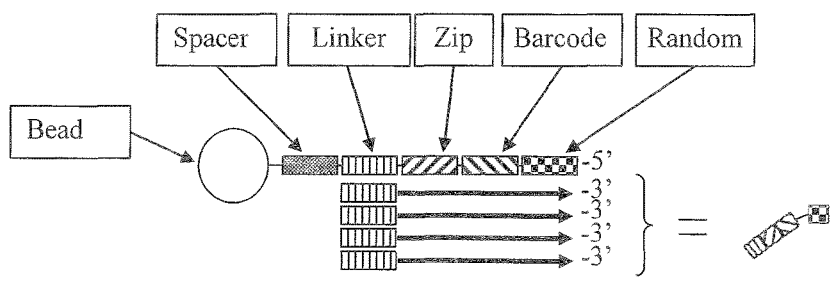
FIG. 3 Depicted is one general example of one aspect of the present invention relating to uses of bead libraries having the structure SURFACE-3'-Spacer-Linker-Zip-Barcode-N(n)-5'. This example of the method uses the beads for the generation of barcoded random primers having a single barcode per emulsion droplet. These barcoded random primers prime the synthesis of droplet-specific, barcoded short sequence reads that can be sequenced using RNA-seq. All five processes, (FIG. 3a) depicts the generation of barcoded random primers by primer extension from the region labeled Linker.
FIG. 3b depicts random primed synthesis from barcoded random primers on full length cDNA molecule(s) trapped in the same emulsion droplet. This is the step in which subsequences of the colocalized target nucleic acid molecule are sampled. These subsequences can be identified as belonging to the same single target nucleic acid molecule because they share the same barcode or a barcode from the same barcode set. If multiple different target nucleic acid molecules are colocalized to the same reaction vessel, they too receive the same barcode or barcode from the same barcode set. Such a case is included as one aspect of the present invention, with the additional consideration that the gene sequences, themselves, can be used in addition to the barcode to (1) group subsequences according to gene sequence, (2) group gene sequences according to barcode. The present invention in some but not all instances cannot distinguish between two target nucleic acid molecules from the same gene that occur in the same reaction vessel, which can be minimized by (1) increasing the number of barcodes available, (2) decreasing the number of target nucleic acid molecules per reaction vessel, (3) increasing the number of reaction vessels in which there is, preferably, one surface per reaction vessel. More than one surface can be present per reaction vessel, but one or zero surfaces per reaction vessel and a sufficient number of reaction vessels that each surface is exposed to preferably only one target nucleic acid molecule from the same gene is preferred.
FIG. 3c depicts additional random priming comprising random primed synthesis from barcoded random primers on denatured products from the previous step. This step results in subsequences of the target nucleic acid molecule flanked in both directions by the sequences of the oligonucleotides generated in FIG. 3a, which comprise PCR amplifiable eDNA products (FIG. 3d), and amplification by PCR (not shown) can occur within each emulsion droplet. The present invention provides in part for emulsion droplets to optimally contain only one of these primer generating beads, and consequently, such that cDNA molecules synthesized within a droplet becomes tagged with the barcode of that single bead. The present invention also provides for, in part, zero or more than one bead per emulsion droplet. When more than one bead is trapped in an emulsion droplet, the same sequence may become tagged with more than one barcode. This can or will lead to double counting, but double counting can be expected to average out over many RNAs and many emulsion droplets. Alternatively, for example, the number of beads per emulsion droplet can be statistically close to zero or one, and can be adjusted to reduce the probability that a single cDNA will be trapped in an emulsion droplet with more than one barcoded bead.
Figure 3B:
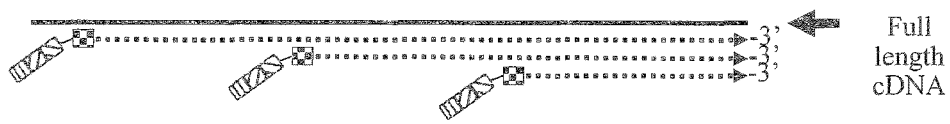
Figure 3C:
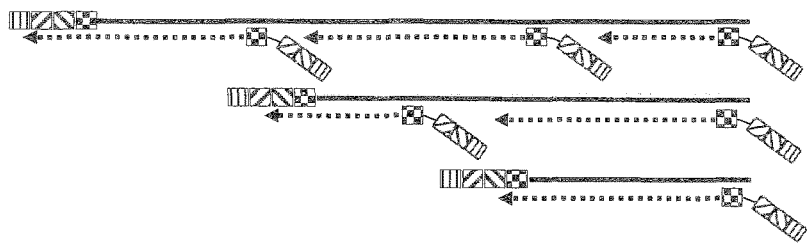
Figure 3D:
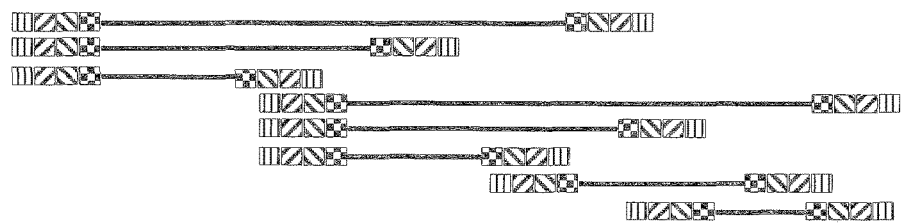
Figure 4A:
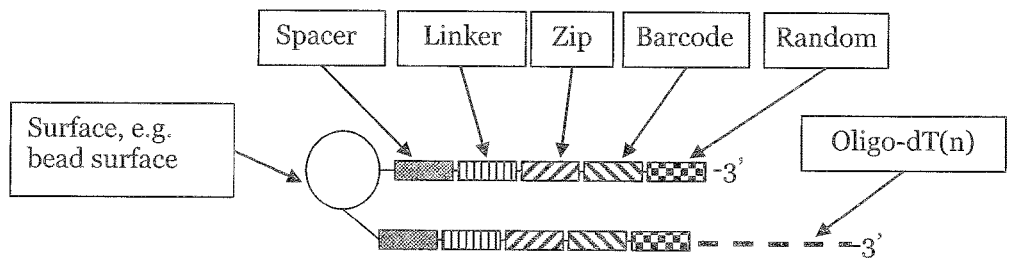
FIG. 4a depicts the structure of barcoded random primers on beads synthesized using reverse synthesis chemistry, with partial oligo-dT(n) single strand ligation, wherein n is a useful length.
Figure 4B:
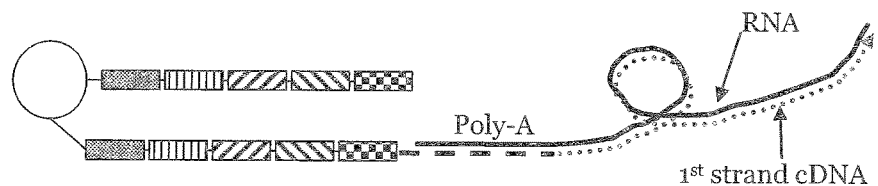
FIG. 4b depicts primer extension from oligo-dT(n) annealed to the poly A tail of an mRNA to prepare first strand cDNA by reverse transcription. If the procedure is performed in an emulsion format, or in multiple reaction vessels of other spatial segregation methods, such as multiple wells in a microtiter plate, the oligo-dT(n) and reverse transcription can be omitted (not depicted), and random primed bridge priming can be initiated at this step using preferably frill length first strand cDNA as the template. Emulsion droplets, microtiter plate wells, capillaries, and other physical configurations that isolate reaction components can be thought of collectively as reaction vessels. When the template is trapped in a reaction vessel, it can remain available for multiple rounds of random priming, and this availability can improve the probability that most or preferably all regions of a full length cDNA will be associated with the barcode from the surface. The DNA synthesis product from this step, i.e. cDNA, becomes covalently attached to the surface in the form SURFACE-5'-Spacer-Linker-Zip-Barcode-N(n)-oligo-dT(n)-cDNA-3' if oligo-dT(n) priming on RNA is used or SURFACE-5'-Spacer-Linker-Zip-Barcode-N(n)-cDNA-3' if priming on cDNA is used.
Figure 4C:
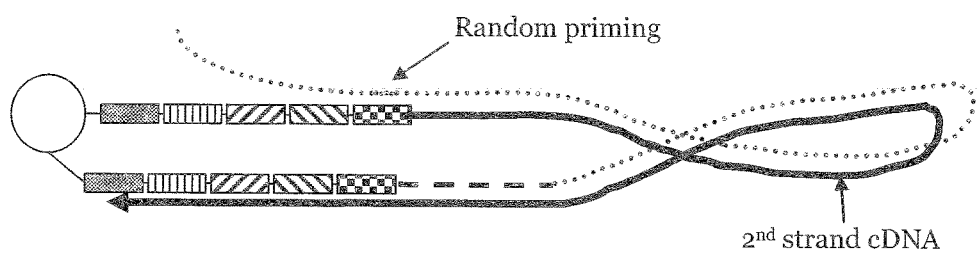
FIG. 4c depicts random primed synthesis on cDNA that is already attached to the surface. Repeated rounds of thermocycling can or will result in multiple random priming events, preferably to sample all or most of the sequence in single molecules and associate those samples with a shared barcode.
Figure 4D:
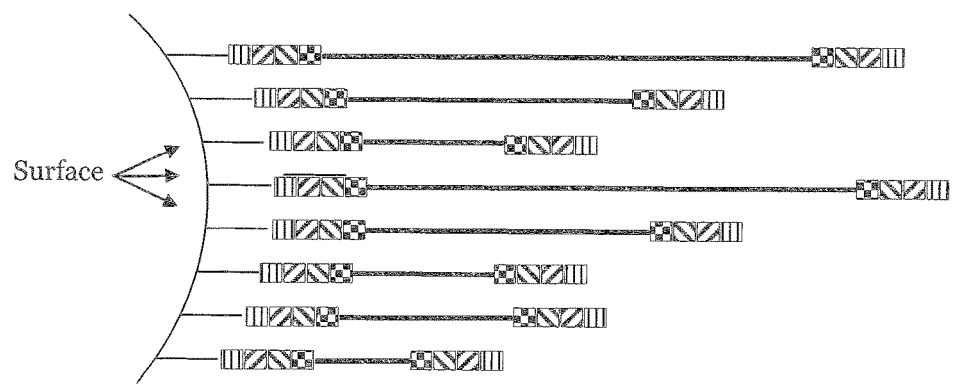
FIG. 4d illustrates the primary product of the foregoing steps, which contain preferably many molecules representing sample sequences templated by the input RNA or DNA flanked by the barcode (and barcode complement). These can be released from the surface by chemical, enzymatic, or other appropriate manipulations, prepared for sequencing and sequenced. Alternatively, the synthesized molecules can be left on the surface and analyzed using hybridization-based methods.

FIG. 2 illustrates the difference between the usual synthesis of a random oligo, and our strategy to ensure that the oligonucleotides can be different between surfaces but identical or nearly identical, or can contain intentional differences, for example, a barcode set, attached to a surface. Nearly identical oligonucleotides can result from errors in synthesis. This non-limiting example assumes a DNA synthesis instrument having four channels and the case in which oligonucleotides are constructed using four possible nucleotides, but different numbers of channels and nucleotides can be used. Standard synthesis chemistry yields SURFACE-5'-Spacer-Linker-Zip-Barcode-N(n)-3', and reverse chemistry yields 5'-Spacer-Linker-Zip-Barcode-N(n)-3'. In this figure, only two cycles for barcode synthesis are illustrated. FIG. 2a illustrates the addition of random nucleotides to the support surface, a bead in this non-limiting example, in the manner used to construct a random sequence oligonucleotide. In this scenario, the beads remain in a single reaction vessel, and each cycle involves the simultaneous presence of all four nucleotide precursors. Consequently, each of the growing oligonucleotides on any single bead acquires a different, randomized oligonucleotide sequence. The present invention, in one aspect, uses the strategy in FIG. 2b, in which all four channels are used, but the beads are pooled and then redistributed between the four channels for every cycle during barcode synthesis. In this scheme, every growing oligonucleotide on any one bead is exposed to a single oligonucleotide precursor on each cycle, but any two beads may experience a different order of exposure to the four nucleotide precursors due to the randomization that occurs upon pooling and redistribution between barcode synthesis steps. Consequently, unlike the case for FIG. 2a, FIG. 2b produces beads which, when considered individually, have only one barcode, but when considered together, have as many barcodes as $4^S$, for the non-limiting case of four possible nucleotides incorporated randomly, where S is the length of the barcode. In FIG. 2a and FIG. 2b, only two cycles are illustrated, for a total barcode complexity of $4^2=16$, for the non-limiting case of four possible nucleotides, but S can be any length, to adjust the number of different barcodes. For example, S=10 results in approximately 1 million barcodes. In one aspect of the present invention, the pooling step can be skipped any number of times, leading to partial randomization, and the pooled beads can be redistributed optionally between 4, 3, or 2 channels, which leads to a more limited form of randomization. The former is useful in identifying synthesis or sequencing errors, in that skipping every other pooling step can be used to create dinucleotide repeats, in which most errors can appear as disruptions in the dinucleotide pattern. For example, if the sequence GGAATTCC is intended, the sequence GGAATCC (i.e. missing a T) can indicate an error in synthesis or sequencing. Likewise, GGAGTTCC (i.e. A misread as a G) indicates a possible sequencing error.

By mixing the beads between synthesis steps, those beads that have the same history will, barring errors in the synthesis reactions, have the same sequence of appended nucleotides to every growing oligonucleotide barcode on the bead, and those with different histories will, barring errors in the synthesis reactions have different barcodes. After synthesis, depending on the number of input beads and the length of the barcode, the ratio of beads with the same barcode to beads with different barcodes is adjustable. For example, if 1e+9 beads are modified, and the length of the barcode is 10 nucleotides, on average there will be approximately 1e+9/1e+6≈1,000 beads with each of 1e+6 barcodes; the 1e+6 comes from the calculation 4 raised to the power 10 is approximately 1 million, i.e. $4^{10}$=1048576, which is an established way of calculating the sequence complexity of a 10 nucleotide long oligonucleotide that is completely random, for the non-limiting case of four possible nucleotides.

Method I. Method for Synthesis of Barcoded Bead Library Using Forward Chemistry

The following non-limiting method provides a series of steps for one non-limiting example of the synthesis of barcoded surfaces with the structure SURFACE-3'-Spacer-Linker-Zip-Barcode-N(n)-5', and assumes the use of four nucleotides G, A, T, and C, although other or additional nucleotides can be accommodated. The individual synthesis steps can be performed in the four channels of a DNA synthesis machine, such as an ABI394, but other instrumentation or manual preparation can also be used.

1. Beads are prepared by standard synthesis to yield the structure SURFACE-3'-Spacer-Linker-Zip-5'. Although only one oligonucleotide is explicitly indicated in this shorthand, it is to be understood here as before that the actual number of oligonucleotides attached per bead is more than one and preferably hundreds, thousands or millions. The length and sequence characteristics of Spacer, Linker, and Zip can be adjusted for different purposes. In one aspect, Linker is chosen to facilitate subsequent sequencing library preparation.
2. The beads are divided into four groups and the oligonucleotides in each group are extended by one nucleotide using one of the 4 bases, G, A, T, or C, to get SURFACE-3'-Spacer-Linker-Zip-G-5', SURFACE-3'-Spacer SURFACE-3'-Spacer-Linker-Zip-T-5', and SURFACE-3'-Spacer-Linker-Zip-C-5'. This synthesis chemistry is run through the deprotection step and stopped.
3. The beads from the previous step are pooled and mixed.
4. Steps 2 and 3 are repeated S times, where S is the length of the Barcode, and in which the length of the barcode increases.
5. Finally, the beads are combined, and the sequence N(n) is added using 4 nucleotides simultaneously.

This method produces beads with the structure SURFACE-3'-Spacer-Linker-Zip-Barcode-N(n)-5'. In principle, the synthesis steps can be achieved using DNA synthesis instrumentation, or can be performed manually.

Method II. Method for Synthesis of Barcoded Bead Library Using Reverse, i.e. Inverted, Chemistry The following non-limiting stepwise procedure achieves the synthesis of barcoded beads with the structure SURFACE-5'-Spacer-Linker-Zip-Barcode$_S$-N(n)-3', and assumes the use of four nucleotides G, A, T, and C, although other or additional nucleotides can be accommodated. The individual synthesis steps can be performed in the four channels of a DNA synthesis machine, such as an ABI394, but other instrumentation or manual preparation can also be used.

1. Beads are prepared by reverse synthesis to yield the structure SURFACE-5'-Spacer-Linker-Zip-3'. Although only one oligonucleotide is explicitly indicated in this shorthand, it is to be understood here as before that the actual number of oligonucleotides attached per bead is more than one and preferably hundreds, thousands or millions. The length and sequence characteristics of Spacer, Linker, and Zip can be adjusted for different purposes. In one aspect, Linker is chosen to facilitate subsequent sequencing library preparation.
2. The beads are divided into four groups and the oligonucleotides in each group are extended by one nucleotide using one of the 4 bases, G, A, T, or C, to get SURFACE-5'-Spacer-Linker-Zip-G-3', SURFACE-5'-Spacer-Linker-Zip-A-3', SURFACE-5'-Spacer-Linker-Zip-T-3', and SURFACE-5'-Spacer-Linker-Zip-C-5'. This synthesis cycle is run through the deprotection step and stopped.
3. The beads in all channels are pooled and mixed.
4. Steps 2 and 3 are repeated S times, where S is the length of the Barcode, and in which the length of the barcode increases.
5. The beads are combined, and N(n) is added in a single channel by using all 4 nucleotides simultaneously.

This produces beads with the structure SURFACE-5'-Spacer-Linker-Zip-Barcode(S)-N(n)-3'.

One aspect of the present invention provides for the use of libraries of surfaces produced by alternative methods to produce surfaces having primers with the structure SURFACE-5'-Spacer-Linker-Zip-Barcode(S)-N(n)-3', such as primer extension or oligonucleotides corresponding to Spacer pre-bound to SURFACE, using complementary sequence 5'-Spacer-Linker-Zip-Barcode(S)-N(n)-5', iterative rounds of primer extension, pooling, and splitting (22), or chemical attachment of individually synthesized oligonucleotides having the structure 5'-Spacer-Linker-Zip-Barcode(S)-N(n)-3' via their 5' end to produce SURFACE-5'-Spacer-Linker-Zip-Barcode(S)-N(n)-3' or having the structure 3'-Spacer-Linker-Zip-Barcode(S)-N(n)-5' to produce SURFACE-3'-Spacer-Linker-Zip-Barcode(S)-N(n)-5'. In addition, splitting, ligation to oligonucleotides containing partial barcodes, pooling, and repeating, can build up large barcodes. Further, utility sequences can be added to the ends by further ligation. Thus, primer extension, direct attachment, and ligation, or a combination thereof can be used to generate libraries as described herein.

The barcodes on a single bead are preferably synthesized accurately, although synthesis errors can result in differences. If S is large enough, no two beads would be expected to have the same barcode sequence. It is not necessary that every bead have a unique barcode. The number of barcodes is an adjustable parameter and preferably should be larger than the number of isoform molecules from any one gene of interest present in an RNA sample to be analyzed. For example, if a gene produces about ten isoform molecules per cell and the analysis sample contains RNA from 100 cells, this implies about 1,000 molecules from that gene in the analysis sample, and assuming Poisson sampling, 4×1,000=4,000 barcodes would give a probability of P(0)=$e^{(-4000/1000)}$≈0.018 that two or more RNA isoforms from the same gene would be tagged with the same barcode. For larger numbers of gene-specific isoforms in an analysis sample, a sufficient number of barcodes are needed to reduce the number of RNA molecules from the same gene becoming associated with the same barcode; such coincidences can interfere with analysis when the targeted molecules comprise two or more isoforms. In eukaryotic cells, abundant transcripts can be represented in, for example, 20,000 copies per cell, possibly representing different isoforms. Using an analysis sample from 100 such cells, suggests the need for 4×2,000,000=8 million barcodes to achieve the same P(0)≈0.018 chance that two isoforms will become associated with the same barcode. Barcodes of 23 nucleotides in length can contain this complexity, when using four nucleotides. Such abundant transcripts may not be of interest, and most eukaryotic cells only contain a few dozen such very abundant transcripts. In such cases, fewer barcodes may be needed. For example, most genes produce transcripts at a rate such that there are fewer than 10 transcripts per cell. For analysis of RNA isoforms from a single cell with P(0)≈0.018, a minimum of 40 barcodes is implied. Fewer barcodes can be used if an analysis sample is divided into multiple analysis samples and prepared in separate reaction containers, including but not limited to separate tubes, wells, or capillaries. In some of the ranges of the present invention, as few as 10 barcodes up to and beyond 10,000,000 can be constructed and may be useful, but such ranges are not limiting as the present invention.

The attachment of random sequences such that every bead contains multiple copies of the same barcode sequence is generally depicted in FIG. 2b. There are 16 barcodes in FIG. 2b because we have illustrated only 2 cycles, but in general, there will be preferably about $4^S$, for the non-limiting case of four possible nucleotides, where S is the number of cycles. After S=10 cycles, there are approximately 1e+6 a barcode, although synthesis errors can alter this. The manufacture of such a barcoded bead library may not be reasonably achieved practically by attaching 1e+6 oligonucleotides post synthetically. One aspect of the present invention permits the synthesis of bead libraries if large barcode complexity at much lower cost than assembling each individual barcoded bead by modifying beads by attachment of individual oligonucleotides. However, for cases in which only rarer transcripts are of interest, including but not limited to mRNA molecules in the about 1-10 copies per mammalian cell, or cases where mRNA molecules from organisms having less complex transcriptome, or cases where mRNA molecule or other nucleic acid molecule collections are known to have lower complexity, or cases where mRNA molecule or other nucleic acid molecule collections may not have lower complexity but those having a low number of copies per cell or sample, then less complex bead libraries can or will be useful, and these can be manufactured by first preparing the nucleic acid component and attaching to the beads post synthetically. This applies to both forward and reverse structures.

Sets of barcodes larger than one can be synthesized on subsets of beads by, for example, randomizing several bases, or for example ligating different sequences to the growing ends of the oligonucleotides on the beads.

Method III. Use of Bead Libraries Having the (Forward Synthesis) Structure SURFACE-3'-Spacer-Linker-Zip-Barcode-N(n)-5'

One non-limiting strategy to construct isoform-informative libraries using SURFACE-3'-Spacer-Linker-Zip-Barcode-N(n)-5' as in FIG. 3. The oligonucleotides bound to the bead serve as templates for the linear amplification of free oligonucleotides having the structure 3'-Linker-Zip-Barcode-N(n)-5' using an oligonucleotide primer that is complementary to Linker, to give the complement, 5'-Linker-Zip-Barcode-N(n)-3'. The latter is, essentially, a "barcoded random primer". This is performed using an emulsion PCR format, arranged so that each emulsion droplet contains, preferably, one or a few full length cDNAs. During multiple thermocycles, consisting of a denaturation step, an annealing step, and an extension step, as used in PCR, three kinds of reactions can or will occur in each emulsion droplet that contains at least one bead and at least one cDNA; the first is linear amplification of the barcoded random primer using the oligonucleotide template attached to the bead, the second is random priming along cDNA or multiple cDNAs, and the third is PCR on random primed products that contain the barcoded product at both ends. The conditions are preferably adjusted to maximize the efficiency of random priming, and the result is a very large collection of emulsion droplets each containing thousands of barcoded random primed products from every full length cDNA, thereby representing most RNAs and preferably every RNA. These products can then be collected, converted to a sequencing library by attachment of appropriate asymmetric adaptors, and sequenced via standard RNA-seq library preparation methods. Analysis includes identification of groups of short sequence reads that share a barcode and assembly of the attached sequences into one or more RNA contigs. The barcode and the transcript-specific sequence fully define a single molecule. The ratio of cDNA to emulsion droplets are arranged so that preferably no two transcripts from the same gene occupy the same emulsion droplet. It is, however, one aspect of the present invention to have more than one transcript per emulsion droplet as long as they are all from different genes.

In the usual RN A-seq strategy, PCR for sample preparation is often avoided because different sequences, as a generality, amplify with different efficiencies. The present invention does not necessarily depend upon uniform PCR amplification efficiencies, such that the mass of the product can be amplified by standard PCR between Linker sequences. In our strategy, we want to increase the chances that a rarely primed sequence will be sampled, even at the expense of over-amplifying one or more other sequence on the same bead. This is acceptable because the quantitative feature from a bead is the yes (1) or no (0) condition associating a barcode with a read, and not the frequency above 1 that this occurs. One, ten or a thousand such events associating BarcodeX with the second exon of GeneX are all counted as 1. The present invention addresses the problem pointed out by Li, et al. (23) that the abundance of an RNA sequence cannot be derived in a simple way by assuming that short sequence reads follow a Poisson distribution with a sequence-independent expected value. Also, the present invention addresses, in part, alternative promoter usage or polyadenylation addition sites in a similar manner as it does alternative splicing. Specifically, in one embodiment the present method yields sequence information on single molecules, including but not limited to different 5'-end and 3'-end sequences of RNAs.

Method IV. Use of Bead Libraries Having the (Reverse Synthesis) Structure SURFACE-5'-Spacer-Linker-Zip-Barcode-N(n)-3'

One non-limiting method to construct isoform-informative libraries is presented in FIG. 4. This method uses oligonucleotides prepared by reverse synthesis. These oligonucleotides initialize randomly primed bridging PCR on the surface of the beads. One variable is the efficiency with which random priming occurs. If one priming event occurs near the 3' end of the RNA sequence, then that sequence is attached to the bead, and additional random priming events are expected in subsequent rounds, preferably with sampling of the entire sequence. To achieve the critical first step, it is helpful to have oligo-dT(n) attached to the surface. This can be achieved by various methods, for example by limited single strand ligation of oligo-dT(n) using T4 RNA ligase I, which can allow first strand extension using reverse transcriptase. The length, n, in oligo-dT(n) can vary preferably within but not limited to the range 10≤n≤30. The present invention also provides, in part, for attachment of oligo-dT (n) by other methods to the surface of the bead, including but not limited to binding chemically, binding to the preexisting oligonucleotides via hybridization, with or without chemical crosslinking, and binding through protein-ligand interactions. Extension from an oligo-dT(n) attached to a bead is known in the art. Oligo-dT(n) as well as other homo- and heteropolymers can or will be attached to the surface or to oligonucleotides or other physical entities, including but not limited to proteins or other chemical entities, already attached to the surface.

As in Method III, distortion of frequencies by PCR presents an issue for the standard library preparation method, but is overcome by certain aspects of the present invention, and therefore the mass of the product can be amplified by standard PCR between Linker sequences. In the usual RNA-seq strategy, PCR for sample preparation is often avoided because different sequences, as a generality, amplify with different efficiencies. Also as in Method III, the method can be optimized to increase the frequency at which a rarely primed sequence can or will be sampled, without incurring a disadvantage from over-amplifying one or more other sequence on the same bead. This is acceptable because the quantitative feature is, in one aspect of the invention, the digital yes (1) or no (0) condition associating a barcode with a read, and not the frequency above 1 that this occurs. For example, one, ten, or a thousand such events associating BarcodeX with the second exon of GeneX are all counted as 1.

Method V. Use of Oligonucleotide Libraries Having the Structure 3'-Linker-Zip-Barcode-N(n)-5'

In a non-limiting variation of Method III, the present invention provides for, in part, the addition of barcoded random primers to multiple cDNA or DNA fragments from single template molecules by combining oligonucleotides having the structure 3'-Linker-Zip-Barcode-N(n)-5', with a PCR primer corresponding to Linker, suitably diluted template molecules, and the other components used in PCR, followed by thermocycling as in PCR in many separate reaction vessels, including but not limited to emulsion droplets, as in emulsion PCR.

This variation differs from Method III in that the barcoded random primers are introduced into the reaction vessels as molecules rather than on surfaces, such as the surfaces of beads. To encourage efficient introduction of barcodes into copies of sub-regions of the template molecules that occupy the same reaction vessel, such as an emulsion droplet, the present invention provides for, in part, linear amplification of 3'-Linker-Zip-Barcode-N(n)-5', the products of which, 5'-Linker-Zip-Barcode-N(n)-3', can preferably engage in random primed synthesis from a single stranded template. To further encourage efficient introduction of barcodes into short copies of the template molecules that occupy the same reaction vessel, the present invention provides for, in part, the introduction of one or more oligonucleotides having the structure 3'-Linker-Zip-Barcode-N(n)-5' into the same emulsion droplet, the multiple copies of which can have, and to a high degree of probability will have, different barcodes.

This method can exploit a chain argument to determine which barcodes, and therefore, which short sequences derived from templates in the same emulsion droplet or other many small reaction vessels. The chain argument is that, if barcodes called X, Y, and Z occur in product molecules in overlapping pairs (X,Y), (Y,Z), then because both X and Y appear with Z, all three barcodes must have been in the same reaction vessel. This allows for more than one barcode to occur in the same reaction vessel. The same argument applies to more than one bead occurring in a single reaction vessel in Method III. Barcodes are preferably sufficiently complex that each isoform molecule present in the sample becomes associated with a non-overlapping subset of barcodes.

As a non-limiting example, emulsion PCR can be arranged with 1 milliliter of aqueous phase, 10 micrometer diameter droplets, containing ~100 copies of a 50 nt long oligonucleotide of the form 3'-Linker-Zip-Barcode-N(n)-5' in which the barcode is 20 nt long, and all other components typical of PCR, including template nucleic acid. During thermocycling, Linker can or will prime synthesis on 3'-Linker-Zip-Barcode-N(n)-5' to make 5'-Linker-Zip-Barcode-N(n)-3', and the random portion of 3'-Linker-Zip-Barcode-N(n)-5' will preferably prime synthesis of first, second, and subsequent copies of subregions of any template molecule in the same emulsion droplet. The barcodes in any one droplet are expected to be, and are preferably, different because the 100 oligonucleotides included in a droplet are drawn from a random population of $4^{20} \approx 1 \text{ exp} 12$. This process results in molecules of the form:

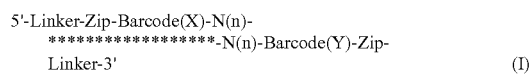
(I)

wherein the asterisks (*) indicate a partial sequence of possibly various lengths of the template taken from preferably random positions at which the random primer part of the oligonucleotide primes synthesis. Note the symbols Barcode(X) and Barcode(Y), which are individual and preferably unique Subsequent rounds of thermocycling can prime within this sequence, thereby producing, for example:

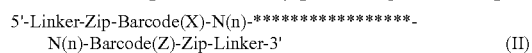
(II)

wherein the product in (I) has been copied into a new product that shares Barcode(X) but has new Barcode(Z). The presence of Barcode(X) and Barcode (Y) in one molecule and the presence of Barcode(X) and Barcode (Z) indicate that all three barcodes can and preferably will, with a high degree of probability, occupy the same emulsion droplet. Another copy of Barcode(X), Barcode(Y), or Barcode(Z) can or will also appear in the a molecule with yet another barcode, such as Barcode(W), as in (III):

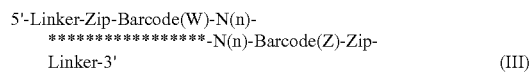
(III)

Because Barcode(Z) is also found paired with Barcode(X) and Barcode(X) is also paired with Barcode(Y) they can and preferably will all, with a high degree of probability, have occupied the same emulsion droplet. Through this arrangement, it can be deduced that the template-derived sequences of any molecules containing Barcode(W), Barcode(X), Barcode(Y), or Barcode(Z) can and preferably will, with a high degree of probability, have been produced within the same emulsion droplet.

The present invention provides for, in part, that the template molecules introduced into this method can be flanked on both ends by sequences that allow PCR amplification to occur preferably simultaneously with barcoded random priming.

The present invention provides, in part, that molecules made using this method can be sequenced, and template molecule sequences inferred by grouping according to barcode, in this case associated via the foregoing transitivity argument, and according to template sequences, themselves, either overlap or matching to a reference sequence, or a combination of both.

General Considerations that Apply to One or More of the Above Methods I-V:
1. Spacer: Spacer length can vary. Optionally, spacers between 0 and 100 nt in length are part of the present invention, but may be longer. This region can or will provide steric relief for primer extension in the vicinity of the surface. Other sequences can be engineered into the Spacer. For example, the spacer can contain restriction endonuclease sites, or RNA promoter sequence.
2. Linker: an adapter to be used as a PCR priming site and for other purposes, including but not limited to attachment of the Y-primers. As with the spacer, other sequences can be engineered into the Linker. For example, the spacer can contain restriction endonuclease sites, or RNA promoter sequence. The length of Linker can be varied optionally, between 0 and 100 nt, and can be longer.
3. Zip: a zip-code for sample identification can be introduced in this position. Introducing zip codes requires an independent synthesis effort for each new zip code. The length of the zip code is discretionary, but can be calculated by $4^N$ where N is the number of samples, for the non-limiting case of four possible nucleotides. For RNA-seq, one nucleotide encoding 4 possibilities can or will distinguish between up to 4 samples sequenced simultaneously. Longer sequences permit error tolerance, such that zip codes 4 nucleotides in length are common and longer zip codes, including but not limited to 4-20 nt are in part provided for by the invention.
4. Barcode: Barcode length can be chosen based on the sequence complexity of the transcriptome to be targeted. 10 nt long barcodes, of which there are $4^{10} \approx 1e+6$ varieties, for the non-limiting case of four possible nucleotides, can or will be appropriate for mammalian transcriptomes, but longer and shorter barcodes are part of the present invention. Preferably, the number of barcodes can or will exceed the number of copies of any single RNA by a large factor. A factor of 4 times as many barcodes as there are molecules from a gene in the analysis sample provides that only ~1.8% of transcripts from that gene will be represented by more than one barcode. For example, in mammals, some transcripts exist in ~1 copy per cell, such that RNA from 1000 cells (i.e. ~2 ng) prompts the use of ~4000 barcodes to reduce the number of transcripts represented by more than one barcode to 1.8%, and there are 4096 barcodes of 6 nt. The estimated average of ~1 copy per cell for most of the complexity of the mammalian transcriptome is an average from a distribution that ranges up to ~100 copies per cell for preferably 90% of the transcriptome complexity and about 50% of the transcriptome mass. Examining transcripts at this level of complexity (i.e. 100 in ~2 ng of RNA) at the 2% error level, prompts the use of ~400,000 barcodes, which corresponds to a barcode length of at least $4^{10}$, for the non-limiting case of four possible nucleotides. FIG. 2 provides for a method by which this level of barcode complexity can be achieved in ten steps. Consequently, barcodes can vary optionally, and values in the neighborhood of 10 can or will be useful in this range of transcript complexity. An additional issue is that errors during reading barcodes can or will result in spurious overlap of contigs. Longer barcodes reduce this problem. Also, longer barcodes are more permissive of larger input RNA or DNA amounts. It is one aspect of the present invention to introduce more than one barcode per bead, and this is referred to as a barcode set. For example, a barcode can be introduced that contains one or more degenerate positions. In such a case, preferably the barcodes can or will contain some characteristic that defines them as a barcode set, so that the single molecule origin of DNA molecules associated with any member of the set can be assessed. This is not required in certain instances, such as but not limited to the case where each individual barcode becomes associated with sufficient sequence information to reconstruct the isoform. Bead libraries can also be made by attaching pre-made oligonucleotides to beads, one or more at a time. In this case, a barcode set can contain one or more specific sequences that are attached to the same bead, and there need be no sequence similarity between sequences, but a record of, or an appropriate method of identifying the members of the barcode set. A barcode set can, therefore, contain one or more sequences.
5. Random primer: Efficient random priming can be achieved using N(n), but one can increase this length to encourage more frequent priming. Also, some non-randomness can be included in a random primer sequence to obtain specific purposes. For example, one can include two purines at the 3' end to discourage primer dimer formation on the bead surface.
6. Inclusion of the random primer portion of the sequence is optional. One can, for example, target a specific gene with this region, e.g. using beads having the structure SURFACE-3'-Spacer-Linker-Zip-Barcode-Specific-5' or SURFACE-5'-Spacer-Linker-Zip-Barcode-Specific-3', where Specific indicates primers targeting one or more gene regions.
7. The present invention provides, in part, for amplification of nucleic acids after the barcodes are introduced, by any appropriate method including but not limited to PCR, rolling circle amplification, linear amplification, and combinations thereof
8. The present invention provides, in part, for the use of other nucleic acids, such as but not limited to oligonucleotide primers, oligonucleotide primers any part of which is introduced or becomes double-stranded.
9. The present invention provides, in part, for the use of enzymes and proteins, including but not limited to RNA polymerase, DNA polymerase, restriction endonucleases, carrier proteins, albumin, and single stranded binding proteins.
10. The present invention also provides, in part, for the use of small molecules, such as nucleotides, non-standard nucleotides, soaps, detergents, oils, salts, counter ions, fluorescent molecules, radionuclides, and other organic molecules, which may or may not influence the reactions or reaction products.
11. In some DNA synthesis methods, larger yields of oligonucleotides on beads can be achieved using a polymer, rather than a glass, support. The present invention provides for in part releasing the oligonucleotides and extended products from the beads by chemical, enzymatic, or other appropriate methods. The present invention also includes but is not limited to not releasing the oligonucleotides and extended products from the beads and combining these beads with some other analysis method, such as hybridization to a fluorescent probe.

Data Analysis:

short sequence read alignment programs can be used to align the reads using software, including but not limited to the software programs bowtie2 (24) and cufflinks (25). Databases of known RNA sequences can be used to build contigs, and databases of genomic sequence can be used to identify contigs for which there is no known or suspected corresponding RNA isoform. Raw sequence files can be processed to index records according to barcode. Each transcriptome-derived short sequence read associated with the same barcode is assembled into one or more contigs. Multiple RNA sequences can or will have the same barcode, whereas when two or more RNAs from the same gene have the same barcode, this can lead to the analysis problem illustrated in FIG. 1. The present invention provides in part a method to quantify RNA isoforms, and can or will also quantify RNAs for which there may be only one isoform, or for which the isoform model can be identified from short sequence reads.

Extension to Genomic Sequencing:

The present invention also provides for in part analysis of genomic DNA, specifically sequences that are repeated in the genome but can contain some differences. The present invention in part provides for the use of beads or other surfaces having the configuration SURFACE-3'-Spacer-Linker-Zip-Barcode-N(n)-5' or SURFACE-5'-Spacer-Linker-Zip-Barcode-N(n)-3' to analyze the structure of nucleic acids, whether RNA or DNA. In some aspects of the invention, the molecule of interest is DNA. One difficulty in analyzing DNA occurs when chromosomal DNA contains multiple regions having similar but different structures. This situation can arise when regions contain sub-sequences that are smaller than the genomic sequencing read length. As with mRNA isoforms, some configurations of repeated sequences cannot be deconvoluted from short sequence reads. The present invention provides in part for exposure of such sequences to beads or surfaces having the structure SURFACE-3'-Spacer-Linker-Zip-Barcode-N(n)-5' or SURFACE-5'-Spacer-Linker-Zip-Barcode-N(n)-3' to generate multiple barcoded short sequence reads from individual molecules.

Further Preferred Aspects of the Present Invention

I. A Library of Surfaces to which the Surfaces are Attached One or More Oligonucleotides by One or More Oligonucleotide Linkers.

One aspect of the present invention is a library of surfaces to which surfaces are attached one or more oligonucleotides by one or more oligonucleotide linkers, including: a) a plurality of surfaces; b) a plurality of oligonucleotides, including: 1) one or more oligonucleotide barcodes operably attached to the 3' end of the oligonucleotide linkers; and 2) a randomized or partially randomized oligonucleotide sequence operably linked to the 3' end of the oligonucleotide barcodes; wherein the oligonucleotide linkers are operably linked to a surface by way of their 5' end; and further wherein the oligonucleotide barcodes comprise one or more distinct barcodes or barcode sets per surface.

In this aspect of the present invention, the 3'-end of the oligonucleotides are available for primer extension, allowing for the randomized bases at the 3'-end to prime nucleic acid synthesis at preferably multiple sites within a target molecule. In this library, the number of barcodes attached to a multitude of surfaces is preferably large, and preferably greater than the total number of target nucleic acid molecules that have different sequences; two nucleic acid molecules have different sequences when any aspect of their sequence differs. For example, two RNA isoforms from the same gene may differ due to inclusion of different exons, use of different promoters, or use of different polyadenylation sequences. As a further example, two nucleic acid molecules from genomic DNA are different if they differ at one or more base pair. A preferred aspect of the present invention is to associate one or more target nucleic acid molecules with one barcode in such a way that no two identical target nucleic acid molecules are associated with the same barcode, and in such a way that no two target nucleic acid molecules transcribed from the same gene or derived from the same genomic location are associated with the same barcode. A further aspect of the present invention is that more than one barcode can be associated with a single target molecule if (1) the barcodes are members of a barcode set, and therefore identifiable as bound to the same surface, or (2) two or more barcodes can be identified as belonging to the same surface due to inclusion in the same product molecule. In this case, sequences can be reassembled using a chain rule, which is described above.

In another aspect of the present invention, the oligonucleotide linkers are attached to the surfaces via one or more oligonucleotide spacers. The spacers and linkers are both utility sequences. Spacers can be included to set the rest of the oligonucleotide away from the surface to allow steric access by enzymes to the linker sequence. As such, there is no requirement that the spacer have a specific sequence, or even that it comprise nucleic acid, as other polymers can, in principle, provide steric relief. The Linker comprises one or more sequences that must be know, such that oligonucleotides having complementarity to the Linker can be designed.

In a further aspect of the present invention, the said surfaces include but are not limited to: a glass, a magnetic material, a plastic, a polymeric material, a ceramic, a composite, a biopolymeric material (including but not limited to a nucleic acid, a condensed nucleic acid, a peptide, a protein, or a combination thereof), or a combination thereof.

In an additional non-limiting aspect of the present invention, the surfaces are spherical, substantially spherical in shape, or a combination thereof. More complex surfaces can be produced by methods including but not limited to lithography, cutting, stamping, molding, precipitating, polymerizing, depositing, disrupting or coagulating, or a combination thereof.

In another aspect of the present invention, also includes one or more zip-code sequence adjacent to the barcodes or barcode sets. Zip code sequences can be useful to distinguish between entire experiments, when DNA products produced using aspects of the present invention are combined and sequenced. In such a case, zip codes can be used to distinguish between sequences analyzed from two or more samples.

In a further aspect of the present invention, one or more of the oligonucleotides are extended with oligo-dT, oligo-dA, or a combination thereof. These can be thought of as utility sequences. A further aspect of the present invention provides for methods to capture mRNA or first strand cDNA, or other sequence, on a surface. Capturing in this manner brings the mRNA or first strand cDNA, or other sequence, into proximity with the barcoded random primer oligonucleotides also on the surface. These utility sequences can be attached enzymatically, using ligation, primer extension, terminal transferase or poly-A polymerase. A further aspect of the present invention also provides for attaching such a utility sequence directly to the surface, such as by chemical binding using any of a wide variety of chemical methods known in the art.

In another aspect of the present invention, one or more of the oligonucleotides are extended with a specific or selected sequence. Similarly to extension using poly-dT or poly-A, a further aspect of the present invention provides for attachment of a specific or selected sequence for the purpose of capturing specific molecules. This can be done to determine the isoform structures, such as but not limited to mRNA isoforms, associated with a specific subsequence, such as the different mRNA isoforms produced by a given gene.

Although specific mRNA capture is known to the art, capturing a specific mRNA and associating its subsequences with barcodes in order to define the detailed sequence of one or more individual target molecules is unique.

II. A Method of Using the Library Exemplified but not Limited to Section I to Attach a Barcode to One or More Oligonucleotide Subsequences within a Target Nucleic Acid Molecule.

A second aspect of the present invention is a method of using the library exemplified but not limited to section I to attach a barcode to one or more oligonucleotide subsequences within a target nucleic acid molecule, including: a) annealing the 3'-end of the oligonucleotides on a surface of exemplified but not limited to section I to random positions in a target nucleic acid molecule to create an annealed oligonucleotide on said surface; b) enzymatic primer extension of the annealed oligonucleotides to synthesize one or more double-stranded subsequences of the target nucleic acid molecule; c) denaturation of the one or more double-stranded subsequences; and d) repetition of steps a-c one or more times to introduce the same barcode or a barcode from the same barcode set to one or more subsequences of the same target nucleic acid molecule.

In this aspect of the present invention, the 3'-ends of the barcoded random primers are available for annealing to the target nucleic acid molecule either bound to the surface via oligo-dT, oligo-dA, or a specific oligonucleotide extension, or colocalized with the surface in a reaction vessel, and the annealed 3'-ends of the barcoded random primers can be enzymatically extended. Both annealing and extension can, if desired, be repeated multiple times by using alternate rounds of annealing, extension and denaturation. This associates one or more preferably overlapping subsequences with the colocalized barcode or barcodes. By determining the sequences of the subsequences and grouping the subsequences based on barcode and gene-specific sequence, one can determine the sequences of the target nucleic acid molecules on a molecule-by-molecule basis. This resolves or partially resolves the problem of constructing a correct or largely correct isoform model.

In another aspect of the present invention, multiple nucleic acid molecules are distributed over a plurality of the surfaces. When two target nucleic acid molecules that derive from the same gene or genomic location become associated with the same barcode, analysis for different isoforms can be hindered. A further aspect of the present invention provides for distribution of target nucleic acid molecules over a plurality of surfaces having largely different barcodes, such that the probability of two such related molecules are unlikely to be colocalized to the same surface or the same reaction vessel.

In a further aspect of the present invention, the target nucleic acid molecule is captured on the surface by said oligo-dT operably linked directly or indirectly to the surface, by the oligo-dA operably linked directly or indirectly to the surface, or a combination thereof. In this method, target nucleic acid molecules can be bound to a surface using oligo-dT. This aspect of the present invention is particularly useful to capture mRNA having polyadenylated tails. Following binding, the oligo-dT can be extended using reverse transcriptase. This has the effect of covalently attaching the complement of the target nucleic acid to the surface. Such attachment creates close proximity between the target nucleic acid cDNA and the barcoded random primers also attached to the surface. This can be done prior to emulsification, or in emulsion droplets. The same arguments apply to using oligo-dA to capture first strand cDNA after first strand cDNA production by extension of a free oligo-dT primer.

In an additional aspect of the present invention, the target nucleic acid molecule is captured on the surface by the specific or selected sequence operably linked directly or indirectly to the surface. The present invention provides in part for a method to limit the number of sequences and subsequences interacting with said oligonucleotides on a surface or in a reaction vessel to a predetermined set, prior to studying detailed target nucleic acid molecule structure. Additionally, prebinding of a predetermined set to the oligonucleotides on a surface, followed by washing unbound nucleic acid molecules from the surfaces has the effect of enriching for the target molecules, the latter potentially improving on sequence analysis efficiency.

In another aspect of the present invention, reactions are performed in multiple separate reaction vessels. This distinction is made because the method can be performed either in multiple separate reaction vessels or in a packed column wherein the beads are not allowed to mix freely. Also, after primer extension from oligo-dT or oligo-dA in which first strand cDNA or a complement thereof is physically attached to a surface, subsequent reactions can be performed in any configuration that limits contact between surfaces, such as high dilution, physical attachment of the surfaces to a larger surface, trapping on a surface such as a membrane or glass filter, or distribution in one or more long capillaries.

In a further aspect of the present invention, the reaction vessels include wells, test tubes, or droplets.

In an additional aspect of the present invention, reactions are performed in the aqueous phase droplets in an emulsion. Preferred reaction vessels include but are not limited to emulsion droplets, microtiter plates, micro tubes, capillaries, and aqueous droplets deposited on glass or plastic slides or in micro-reaction chambers.

In a further aspect of the present invention, further including the addition of inert surfaces. Inert surfaces, including but not limited to beads with inert surfaces, can be used to separate the active surfaces of the library from one another. The present invention provides in part for performing extension reactions in a packed column with inert surfaces separating active surfaces, such that the frequency of contact of a single target nucleic acid molecule with more than one surface, and therefore more than one barcode, can be reduced, minimized or otherwise controlled.

In an additional aspect of the present invention, reactions are performed in a column of the surfaces or packed surfaces. As explained above, inert surfaces, including but not limited to beads with inert surfaces, can be used to separate the active surfaces of the library from one another. The present invention provides for in part performing extension reactions in a packed column with inert surfaces separating active surfaces, such that the frequency of contact of a single target nucleic acid molecule with more than one surface is reduced or minimized.

In another aspect of the present invention, the enzymatic primer extension is performed using a reverse transcriptase. As explained above, the present invention provides for in part synthesis of first strand cDNA via capture of mRNA by oligo-dT, followed by first strand cDNA synthesis by extension of the annealed oligo-dT using reverse transcriptase.

In a further aspect of the present invention, the enzymatic primer extension is performed using a DNA polymerase. The method provides for synthesis of DNA by primer extension using as primers oligo-dA, a specific sequence, or the random end of the barcoded random primers attached to the surfaces. Note that the aforementioned reverse transcriptase is also a DNA polymerase.

In an additional aspect of the present invention, also includes determining the sequence of the nucleic acid molecules produced by the method. The linker sequence can be tailored to facilitate sequencing library construction.

In another aspect of the present invention, the nucleic acid molecules produced by the method that share a barcode or barcode set are assembled into one or more contiguous sequences. An objective in molecular biology is to describe and analyze sequences. The present invention provides in part and in one aspect for the construction of sequencing libraries in such a manner that subsequences of individual target nucleic acid molecules are tagged with the same or related barcodes to allow subsequences of an individual target nucleic acid molecule to be identified via contiguous barcode or barcodes.

In a further aspect of the present invention, the nucleic acid molecules produced by the method having different sequences are analyzed. Analysis includes but is not limited to determining the sequence or partial sequence of individual target nucleic acid molecules, and counting the number of each distinct nucleic acid target molecule.

III. A Library of Surfaces to which the Surfaces are Attached One or More Oligonucleotides by One or More Oligonucleotide Linkers A third aspect of the present invention is a library of surfaces to which the surfaces are attached to one or more oligonucleotides by one or more oligonucleotide linkers, including: a) a plurality of surfaces; b) a plurality of oligonucleotides, including: 1) one or more oligonucleotide barcodes operably attached to the 5' end of the oligonucleotide linkers; and 2) a randomized or partially randomized oligonucleotide sequence operably linked to the 5' end of said oligonucleotide barcodes; wherein the oligonucleotide linkers are operably linked to a surface by way of their 3' end; and further wherein the oligonucleotide barcodes include one or more distinct barcodes or barcode sets per surface.

This library is similar to that described above, except that the oligonucleotides bound to the surface are bound by the 3'-end rather than by the 5'-end. This has consequences regarding the methods that it enable as set forth herein.

In another aspect of the present invention, the oligonucleotide linkers are attached to the surfaces via one or more oligonucleotide spacers. As above, the spacers and linkers are both utility sequences. Spacers can be included to set the rest of the oligonucleotide away from the surface to allow steric access by enzymes to the linker sequence. As such, in one aspect of the present invention there is no requirement that the spacer have a specific sequence, or even that it comprise nucleic acid, as other polymers can, in principle, provide steric relief. The Linker in this aspect of the present invention comprises one or more sequences that must be know, such that oligonucleotides having complementarity to the Linker can be designed.

In a further aspect of the present invention, the surfaces include but are not limited to: a glass, a magnetic material, a plastic, a polymeric material, a ceramic, a composite, a biopolymeric material (including but not limited to a nucleic acid, a condensed nucleic acid, a peptide, a protein, or a combination thereof); or a combination thereof.

In an additional aspect of the present invention, the surfaces are spherical, substantially spherical in shape, or a combination thereof. As above, additional and possibly more complex surfaces can be produced by methods including but not limited to lithography, cutting, stamping, molding, precipitating.

In a further aspect of the present invention, also including one or more zip-code sequence adjacent to said barcodes or barcode sets. Zip code sequences can be useful to distinguish between entire experiments, when DNA products produced using certain aspects of the present invention are combined and sequenced. In such a case, zip codes can be used to distinguish between sequences analyzed from two or more samples.

IV. A Method of Using the Library Exemplified but not Limited to Section III to Attach a Barcode to One or More Subsequences within a Target Nucleic Acid Molecule A fourth aspect of the present invention is a method of using the library exemplified but not limited to section III to attach a barcode to one or more subsequences within a target nucleic acid molecule, including: a) co-localizing in at least one reaction vessel: (i) at least one surface of said library with, (ii) a target nucleic acid molecule, (iii) a linker primer, (iv) a thermostable DNA polymerase, (v) reagents for DNA synthesis; b) theromocycling to produce: (i) linear amplification of the complement of said oligonucleotide attached to said surface, and (ii) sampling of the co-localized nucleic acid by annealing and extension of said complement.

The present invention, in one aspect, provides for a closely related but distinct method for introduction of a barcode into subsequences of the same molecule. In this aspect of the invention, surfaces serve to deliver multiple copies of the same or related barcoded random primer sequences to multiple reaction vessels. These multiple copies then serve as templates for linear amplification, thereby producing many copies of the barcoded random primers per reaction vessel. In this embodiment of the present invention, the surface-bound oligonucleotides are bound via their 3' ends; consequently, in this orientation, the surface-bound oligonucleotides cannot serve as primers. However, they can and will serve as templates to produce multiple free-floating barcoded random primers. The previous method discussed above provides for oligonucleotides bound to the surface via their 5'-ends, thereby allowing random priming reactions to occur strictly on the surface. In this aspect of the present invention, surfaces and target molecules are preferably colocalized in reaction vessels.

In another aspect of the present invention, multiple nucleic acid molecules are preferably colocalized with the surfaces in a multiple separate reaction vessels. For this aspect of the present invention, free-floating barcoded random primers are synthesized, and therefore the surfaces must be colocalized with the target nucleic acid molecules within individual reaction vessels; methods involving packed beads and colocalization on surfaces are precluded. So also is chemical denaturation: here thermocycling is preferably used.

In a further aspect of the present invention, the target nucleic acid includes DNA. First strand cDNA can be used as a template, as can genomic DNA.

In an additional aspect of the present invention, also included is the addition of reverse transcriptase. Reverse transcriptase can be added to the reaction vessel to produce cDNA in situ.

In another aspect of the present invention, DNA is synthesized in situ using reverse transcriptase. As above, reverse transcriptase can be added to the reaction vessel to produce cDNA in situ.

In a further aspect of the present invention, the reaction vessels includes the aqueous phase droplets in an emulsion.

In an additional aspect of the present invention, the reaction vessels includes wells, test tubes, droplets, or a combination thereof. For this method, multiple surfaces are preferably distributed among multiple reaction vessels.

In another aspect of the present invention, also includes determining the sequence of the nucleic acid molecules produced by the method. The linker sequence can be tailored to facilitate sequencing library construction.

In a further aspect of the present invention, also includes determining the sequence of the nucleic acid molecule produced by the method. An objective in molecular biology is to describe and analyze sequences. The present invention provides for in part the construction of sequencing libraries in such a manner that subsequences of individual target nucleic acid molecules are tagged with the same or related barcodes to allow subsequences of an individual target nucleic acid molecule to be identified via contiguous barcode or barcodes.

In an additional aspect of the present invention, the nucleic acid molecules produced by the method that share a barcode or barcode set are assembled into one or more contiguous sequences.

In another aspect of the present invention, the nucleic acid molecules produced by the method having different sequences are analyzed. Analysis includes but is not limited to determining the sequence or partial sequence of individual target nucleic acid molecules, and counting the number of each distinct nucleic acid target molecule.

LITERATURE CITED

1. Wang K, Singh D, Zeng Z, Coleman S J, Huang Y, Savich G L, et al. MapSplice: accurate mapping of RNA-seq reads for splice junction discovery. Nucleic Acids Res. 2010; 38:e178. PMID20802226.
2. Pan Q, Shai O, Lee L J, Frey B J, Blencowe B J. Deep surveying of alternative splicing complexity in the human transcriptome by high-throughput sequencing. Nat Genet. 2008; 40:1413-5. PMID18978789.
3. Wang E T, Sandberg R, Luo S, Khrebtukova I, Zhang L, Mayr C, et al. Alternative isoform regulation in human tissue transcriptomes. Nature. 2008; 456:470-6. PMID18978772.
4. Oltean S, Bates D O. Hallmarks of alternative splicing in cancer. Oncogene. 2013. PMID24336324.
5. Jiang H, Wong W H. Statistical inferences for isoform expression in RNA-Seq. Bioinformatics. 2009; 25:1026-32. PMID19244387.
6. Hiller D, Jiang H, Xu W, Wong W H. Identifiability of isoform deconvolution from junction arrays and RNA-Seq. Bioinformatics. 2009; 25:3056-9. PMID19762346.
7. Hiller D, Wong W H. Simultaneous isoform discovery and quantification from RNA-seq. Statistics in biosciences. 2013; 5:100-18. PMID23888185.
8. LeGault L H, Dewey C N. Inference of alternative splicing from RNA-Seq data with probabilistic splice graphs. Bioinformatics. 2013; 29:2300-10. PMID23846746.
9. Nariai N, Hirose O, Kojima K, Nagasaki M. TIGAR: transcript isoform abundance estimation method with gapped alignment of RNA-Seq data by variational Bayesian inference. Bioinformatics. 2013; 29:2292-9. PMID23821651.
10. Hu Y, Huang Y, Du Y, Orellana C F, Singh D, Johnson A R, et al. DiffSplice: the genome-wide detection of differential splicing events with RNA-seq. Nucleic Acids Res. 2013; 41:e39. PMID23155066.
11. Trapnell C, Pachter L, Salzberg S L. TopHat: discovering splice junctions with RNA-Seq. Bioinformatics, 2009; 25:1105-11. PMID19289445.
12. Kim D, Pertea G, Trapnell C, Pimentel H, Kelley R, Salzberg S L. TopHat2: accurate alignment of transcriptomes in the presence of insertions, deletions and gene fusions. Genome Biol. 2013; 14:R36. PMID23618408.
13. Fullwood M J, Wei C L, Liu E T, Ruan Y. Next-generation DNA sequencing of paired-end tags (PET) for transcriptome and genome analyses. Genome Res. 2009; 19:521-32. PMID19339662.
14. Bani-Yaghoub M, Kubu C J, Cowling R, Rochira J, Nikopoulos G N, Bellum S, et al. A switch in numb isoforms is a critical step in cortical development. Dev Dyn. 2007; 236:696-705. PMID17253625.
15. Lapuk A V, Volik S V, Wang Y, Collins C C. The role of mRNA splicing in prostate cancer. Asian journal of andrology. 2014; 16:515-21. PMID24830689.
16. Mina R D, Butty V L, Shendure J, Williams B R, Housman D E, Church G M. Digital genotyping and haplotyping with polymerase colonies. Proc Natl Acad Sci USA. 2003; 100:5926-31. PMID12730373.
17. Tiemann-Boege I, Curtis C, Shinde D N, Goodman D B, Tavare S, Arnheim N. Product length, dye choice, and detection chemistry in the bead-emulsion amplification of millions of single DNA molecules in parallel. Anal Chem. 2009; 81:5770-6. PMID19601653.
18. Shendure J, Porreca G J, Reppas N B, Lin X, McCutcheon J P, Rosenbaum A M, et al. Accurate multiplex polony sequencing of an evolved bacterial genome. Science. 2005; 309:1728-32. PMID16081699.
19. Fellmann F, Pretet J L, Fellmann D. Simplified protocol of solid-phase cDNA libraries for multiple PCR amplification. Biotechniques. 1996; 21:766, 8, 70. PMID8922608.
20. Kojima T, Takei Y, Ohtsuka M, Kawarasaki Y, Yamane T, Nakano H. PCR amplification from single DNA molecules on magnetic beads in emulsion: application for high-throughput screening of transcription factor targets. Nucleic Acids Res. 2005; 33:e150. PMID16214800.
21. Adessi C, Matton G, Ayala G, Turcatti G, Mermod J J, Mayer P, et al. Solid phase DNA amplification: characterisation of primer attachment and amplification mechanisms. Nucleic Acids Res. 2000; 28:E87. PMID11024189.
22. Fan H C, Fu G K, Fodor S P. Expression profiling. Combinatorial labeling of single cells for gene expression cytometry. Science. 2015; 347:1258367. PMID25657253.
23. Li J, Jiang H, Wong W H. Modeling non-uniformity in short-read rates in RNA-Seq data. Genome Biol. 2010; 11:R50. PMID20459815.
24. Langmead B, Trapnell C, Pop M, Salzberg S L. Ultrafast and memory-efficient alignment of short DNA sequences to the human genome. Genome Biol. 2009; 10:R25. PMID19261174,
25. Trapnell C, Williams B A, Pertea G, Mortazavi A, Kwan G, van Baren M J, et al. Transcript assembly and quantification by RNA-Seq reveals unannotated transcripts and isoform switching during cell differentiation. Nat Biotechnol. 2010; 28:511-5. PMID20436464.

All publications, including patent documents and scientific articles, referred to in this application and the bibliography and attachments are incorporate by reference in their entity for all purposes to the extent as if each individual publication were individually incorporated by reference.

All headings are for the convenience of the reader and should not be used to limit the meaning of the text that follow the heading, unless so specified.

What is claimed is:

1. A method of identifying RNA isoforms in a sample comprising:
   (a) co-localizing at least one RNA isoform or its cDNA equivalent with a plurality of at least one barcoded random primer oligonucleotide,
      said barcoded random primer oligonucleotide comprising:
         i) a linker sequence;
         ii) a barcode comprising:
            a nucleic acid sequence distinguishable from the sequences of other barcodes;
         iii) a random primer sequence comprising:
            a nucleic acid sequence containing a degenerate or partially degenerate sequence;
   (b) performing enzymatic primer extension to extend said barcoded random primer sequence from random positions in the co-localized RNA isoform or cDNA equivalent thereby attaching the same barcode to subsequences from all or substantially all exon sequences of said RNA isoform or its cDNA equivalent to form one or more concatenations;
      said one or more concatenations comprising:
         i) said linker sequence;
         ii) said barcode;
         iii) said random primer sequence;
         iv) said exon subsequences of said RNA isoform or said cDNA equivalent
   (c) identifying said RNA isoform by sequencing said barcode and attached exon subsequences.

2. The method of claim 1,
wherein a plurality of RNA isoforms or their cDNA equivalents from the same gene are attached to distinguishable barcodes.

3. The method of claim 1,
wherein a barcode is a member of a barcode set.

4. The method of claim 1, wherein:
   (a) said barcoded random primer oligonucleotides are attached to a plurality of surfaces of a library of surfaces;
   (b) each of said surface is operably attached to a plurality of barcoded random primer oligonucleotides; and
   (c) said barcoded random primer oligonucleotides attached to any single surface have the same barcode or barcodes from the same barcode set.

5. The method of claim 4,
wherein said surface comprises:
   a) a glass;
   b) a magnetic material;
   c) a plastic;
   d) a polymeric material;
   e) a ceramic;
   f) a composite;
   g) a biopolymeric material comprising a nucleic acid, a condensed nucleic acid, a peptide, a protein, or a combination thereof; or
   h) a combination thereof.

6. The method of claim 4,
wherein said surfaces are any shape, spherical, substantially spherical, or a combination thereof.

7. The method of claim 4,
wherein said barcoded random primer oligonucleotides further comprise one or more zip-code sequence adjacent to said barcodes.

8. The method of claim 4,
wherein oligo-dT, oligo-dA, or a combination thereof is attached to said surface directly, or indirectly as part of the attached oligonucleotides.

9. The method of claim 4,
wherein said surface is co-localized with a target nucleic acid molecule by annealing said barcoded random primer oligonucleotides to multiple random positions in the target nucleic acid molecule.

10. The method of claim 4,
wherein multiple nucleic acid molecules are distributed over a plurality of said surfaces.

11. The method of claim 4,
wherein said target nucleic acid molecule is captured on said surface by said oligo-dT operably linked directly or indirectly to said surface, by said oligo-dA operably linked directly or indirectly to said surface, or a combination thereof.

12. The method of claim 4,
further comprising the addition of inert surfaces.

13. The method of claim 4,
wherein reactions are performed in a column of said surfaces or packed said surfaces.

14. The method of claim 4,
wherein said oligonucleotide linkers are attached to said surfaces via one or more oligonucleotide spacers.

15. The method of claim 4, wherein:
   (a) said surface and a target nucleic acid molecule are co-localized in a reaction vessel,
   (b) additional copies of said barcoded random primers are generated by primer extension from the linker sequence.

16. The method of claim 15,
wherein said reaction vessels comprise the aqueous phase droplets in an emulsion.

17. The method of claim 15,
wherein said reaction vessels comprise wells, test tubes, droplets, capillaries or a combination thereof.

18. The method of claim 15,
further comprising, denaturing the product and repeating enzymatic primer extension to introduce the same barcode or a barcode from the same barcode set to additional randomly sampled subsequences of the same target nucleic acid molecule.

19. The method of claim 15,
wherein reactions are performed in multiple separate reaction vessels.

20. The method of claim 15,
wherein the target nucleic acid molecules produced by the method having different sequences are analyzed to determine the ratio of isoforms.

21. The method of claim 1,
wherein said enzymatic primer extension is performed using a reverse transcriptase.

22. The method of claim 1,
wherein said enzymatic primer extension is performed using a DNA polymerase.

23. The method of claim 1,
further comprising determining the sequence of the nucleic acid molecules produced by the method.

24. The method of claim 1,
wherein the target nucleic acid molecules produced by the method that share a barcode or barcode set are assembled into one or more contiguous sequences.

25. The method of claim 1,
wherein the nucleic acid molecules produced by the method having different sequences are analyzed.

26. The method of claim 1, wherein the target nucleic acid molecules produced by the method having different sequences are analyzed to determine the ratio of isoforms.

* * * * *